US006267927B1

(12) United States Patent
Pomar Longedo et al.

(10) Patent No.: US 6,267,927 B1
(45) Date of Patent: Jul. 31, 2001

(54) APPARATUS FOR PERFORMING LABORATORY TESTS AUTOMATICALLY

(75) Inventors: Pere Pomar Longedo, Barcelona; Xavier Pons Munill, Terrassa; Ivan Twose Valls, Barcelona; Enric Alonso Riera, Vilassar; Carlos Restrepo Guerrero, Barcelona; Francesc Pérez Puigdoménech, La Garriga, all of (ES)

(73) Assignee: Grupo Grifols, S.A., Parets del Valles (ES)

( * ) Notice: Subject to any disclaimer, the term of this patent is extended or adjusted under 35 U.S.C. 154(b) by 0 days.

(21) Appl. No.: 09/196,412

(22) Filed: Nov. 19, 1998

(30) Foreign Application Priority Data

| Nov. 19, 1997 | (ES) | 9702412 |
| Nov. 19, 1997 | (ES) | 9702413 |
| Nov. 19, 1997 | (ES) | 9702415 |
| Nov. 19, 1997 | (ES) | 9702514 |

(51) Int. Cl.$^7$ .................................................. G01N 35/10
(52) U.S. Cl. .......................... 422/65; 422/63; 422/64; 422/82.05; 422/100; 436/43; 436/47; 436/48; 436/164; 436/174; 436/180
(58) Field of Search .................... 422/63, 64, 65, 422/82.05; 436/43, 47, 48, 164, 174, 180

(56) References Cited

U.S. PATENT DOCUMENTS

| 3,864,974 | 2/1975 | Rauchwerger | 73/304 C |
| 4,287,155 | 9/1981 | Tersteeg et al. | 422/64 |
| 4,347,741 | 9/1982 | Geiger | 73/304 C |
| 4,434,657 | 3/1984 | Matsumura et al. | 73/304 C |
| 4,444,051 | 4/1984 | Yamaki et al. | 73/304 C |
| 4,478,095 | 10/1984 | Bradley et al. | 73/864.21 |
| 4,595,562 | 6/1986 | Liston et al. | 422/65 |
| 4,912,976 | 4/1990 | Labriola, II | 73/290 R |
| 4,952,518 | * 8/1990 | Johnson et al. | 436/518 |
| 4,961,915 | * 10/1990 | Martin | 422/116 |

(List continued on next page.)

FOREIGN PATENT DOCUMENTS

| 101 580 | 2/1984 | (EP) | G01F 23/26 |
| 0351988A | 1/1990 | (EP) . | |
| 391 861 | 10/1990 | (EP) | G01N 15/04 |

(List continued on next page.)

OTHER PUBLICATIONS

Base De Datos WPIL en QUESTEL, semana 9641, Londres: Derwent Publications Ltd., AN–96407824, Class Q31, S03, JP 08–198226 A (Techno Medica Co. Ltd), resumen.

Primary Examiner—Jill Warden
Assistant Examiner—Kathryn Bex
(74) Attorney, Agent, or Firm—Darby & Darby

(57) ABSTRACT

The apparatus has two main regions of members the operation of which is controlled separately, the first region, to which the user has interactive access, permitting loading of the samples, controls, calibrators, diluents and other equipment for performing the sampling and dilutions and receiving the plate on which the tests are performed, and the second region, to which the user has occasional access, comprising stations dedicated to the rest of the process including incubation, washing, reading, and others, the second region being able to hold several plates at different stages of the process, the apparatus having means for automated movement along three coordinate axes X, Y, Z in order to transport the reagents and the plates in order to complete the process, enabling several tests to be performed at the same time on a set of samples in one or several plates, and enabling new series of tasks with the same or different sets of tests and with the same or different sets of samples to be started when the previous ones have not been completed, the apparatus comprising, beneath its two main regions of members, a series of containers for the storage of the auxiliary liquids of the process and for the collection of washings and waste.

38 Claims, 30 Drawing Sheets

U.S. PATENT DOCUMENTS

| | | | |
|---|---|---|---|
| 5,122,342 | * | 6/1992 | McCulloch et al. .................... 422/65 |
| 5,141,871 | * | 8/1992 | Kureshy et al. ........................ 436/47 |
| 5,158,895 | | 10/1992 | Ashihara et al. ..................... 436/526 |
| 5,207,987 | * | 5/1993 | Kureshy et al. ........................ 422/67 |
| 5,232,665 | * | 8/1993 | Burkovich et al. ..................... 422/65 |
| 5,266,272 | * | 11/1993 | Griner et al. ......................... 422/104 |
| 5,304,347 | * | 4/1994 | Mann et al. ............................ 422/67 |
| 5,443,790 | | 8/1995 | Coeurveille et al. .................. 422/63 |
| 5,546,005 | | 8/1996 | Rauchwerger ....................... 324/688 |
| 5,551,828 | | 9/1996 | Iles ........................................ 414/757 |
| 5,578,269 | * | 11/1996 | Yaremko et al. ....................... 422/64 |
| 5,580,524 | * | 12/1996 | Forrest et al. ......................... 422/63 |
| 5,597,733 | * | 1/1997 | Bell et al. ............................... 436/54 |
| 5,611,240 | | 3/1997 | Yamaguchi ........................ 73/304 C |
| 5,639,425 | * | 6/1997 | Komiyama et al. .................... 422/63 |
| 6,081,326 | * | 6/2000 | Rousseau et al. .................... 356/246 |
| 6,162,399 | * | 12/2000 | Martinell Gisper-Sauch ........ 422/64 |

FOREIGN PATENT DOCUMENTS

| | | | |
|---|---|---|---|
| 0441755A | 1/1991 | (EP) . | |
| 438 159 A1 | 7/1991 | (EP) | ............................. G01F 23/26 |
| 0 517 008 A2 | 12/1992 | (EP) . | |
| 0639774A | 8/1994 | (EP) . | |
| 633 456 A1 | 1/1995 | (EP) | ............................. G01F 23/26 |
| 639 744 A1 | 2/1995 | (EP) | ............................. G01N 35/00 |
| 727 665 A2 | 8/1996 | (EP) | ............................. G01N 35/04 |
| 8704006 | 5/1987 | (ES) | ............................. G01N 35/06 |
| 2 043 022 | 1/1990 | (ES) | ............................. G01N 35/02 |
| 2 075 436 | 4/1992 | (ES) | ............................. G01N 35/02 |
| 2 080 306 | 5/1992 | (ES) | ............................. G01N 35/02 |
| 2 094 377 | 10/1993 | (ES) | ............................. B01L 9/00 |
| 2 647 900 | 12/1990 | (FR) | ............................. G01G 23/26 |
| WO 93/09440 | 5/1993 | (WO) . | |
| WO 93/12431 | 6/1993 | (WO) . | |
| WO 96/24823 | 8/1996 | (WO) | ............................. G01F 23/26 |
| WO 98/58262 | 12/1998 | (WO) | ............................. G01F 23/26 |

* cited by examiner

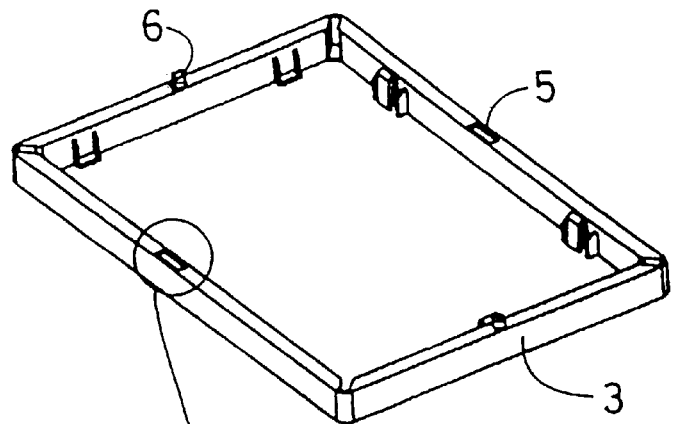
FIG. 2
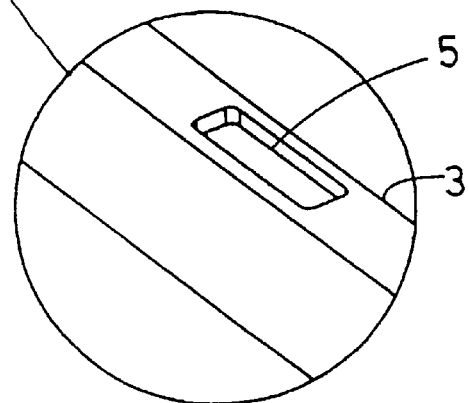
FIG. 2.1
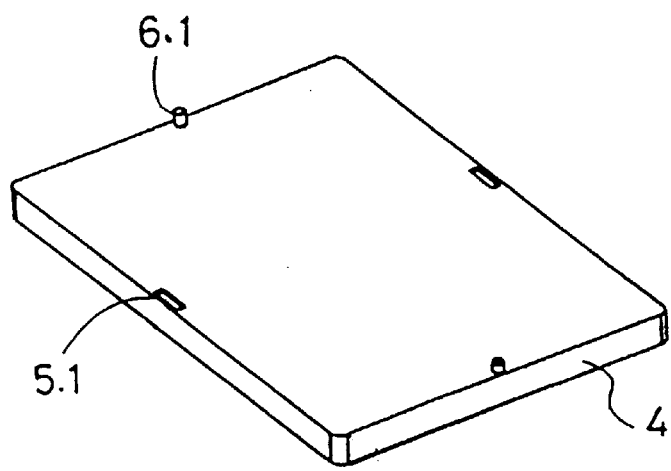
FIG. 2.2

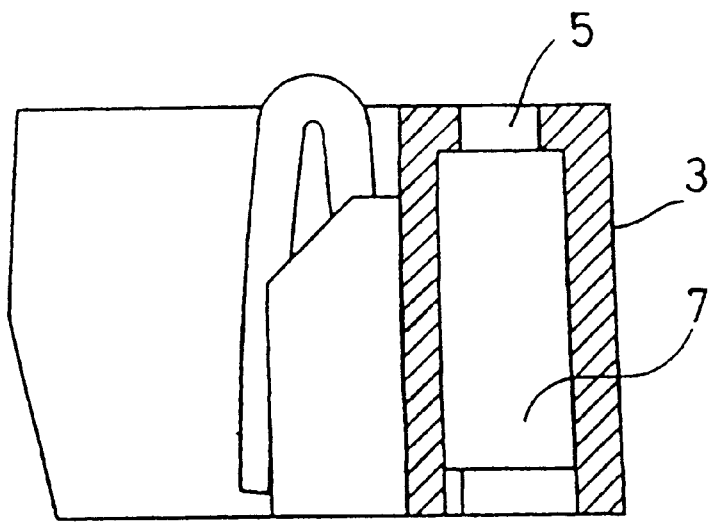
FIG. 2.3
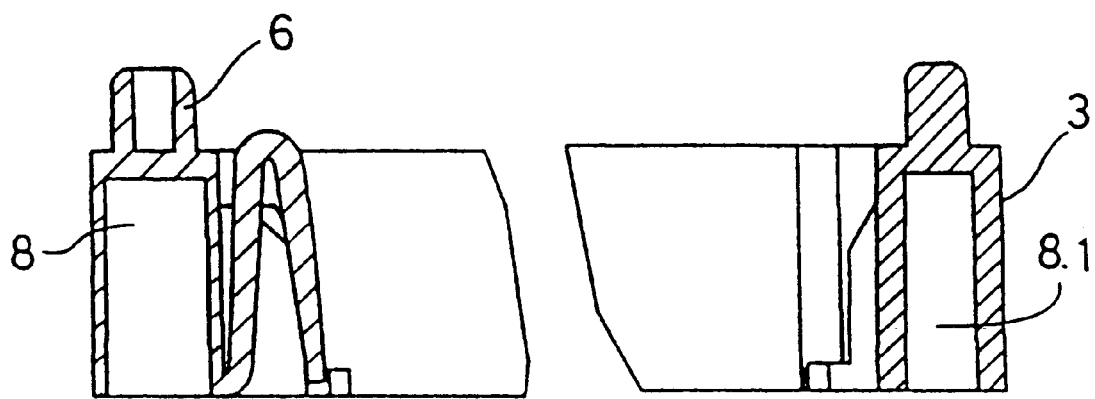
FIG. 2.4

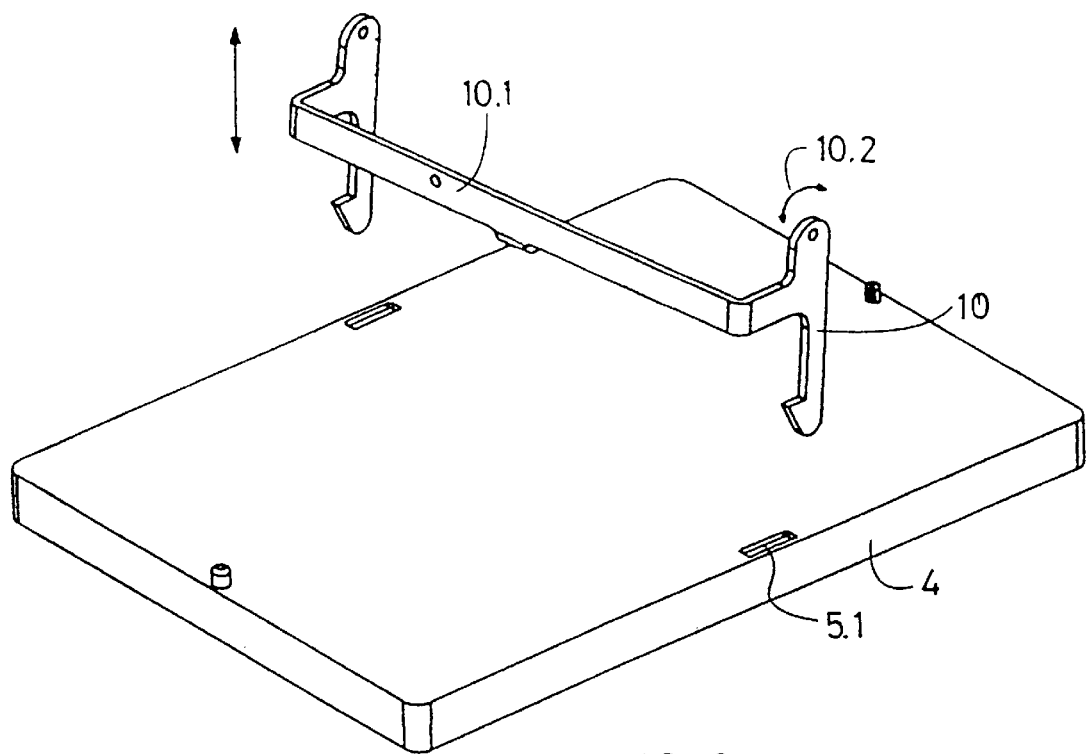
FIG. 3
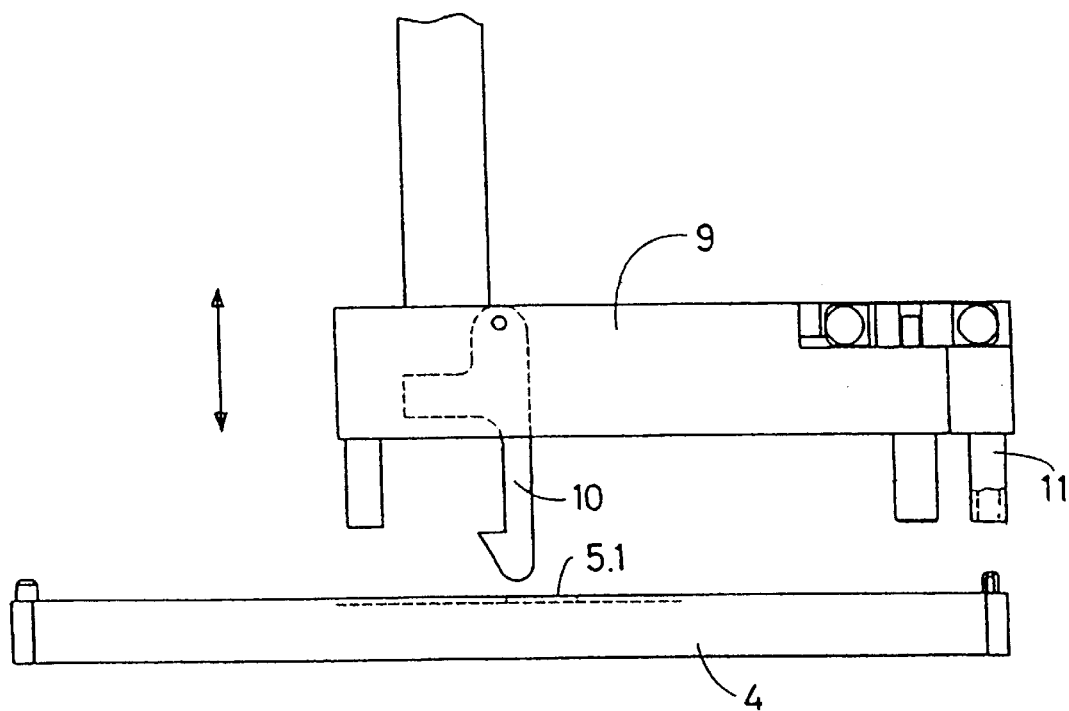
FIG. 3.1

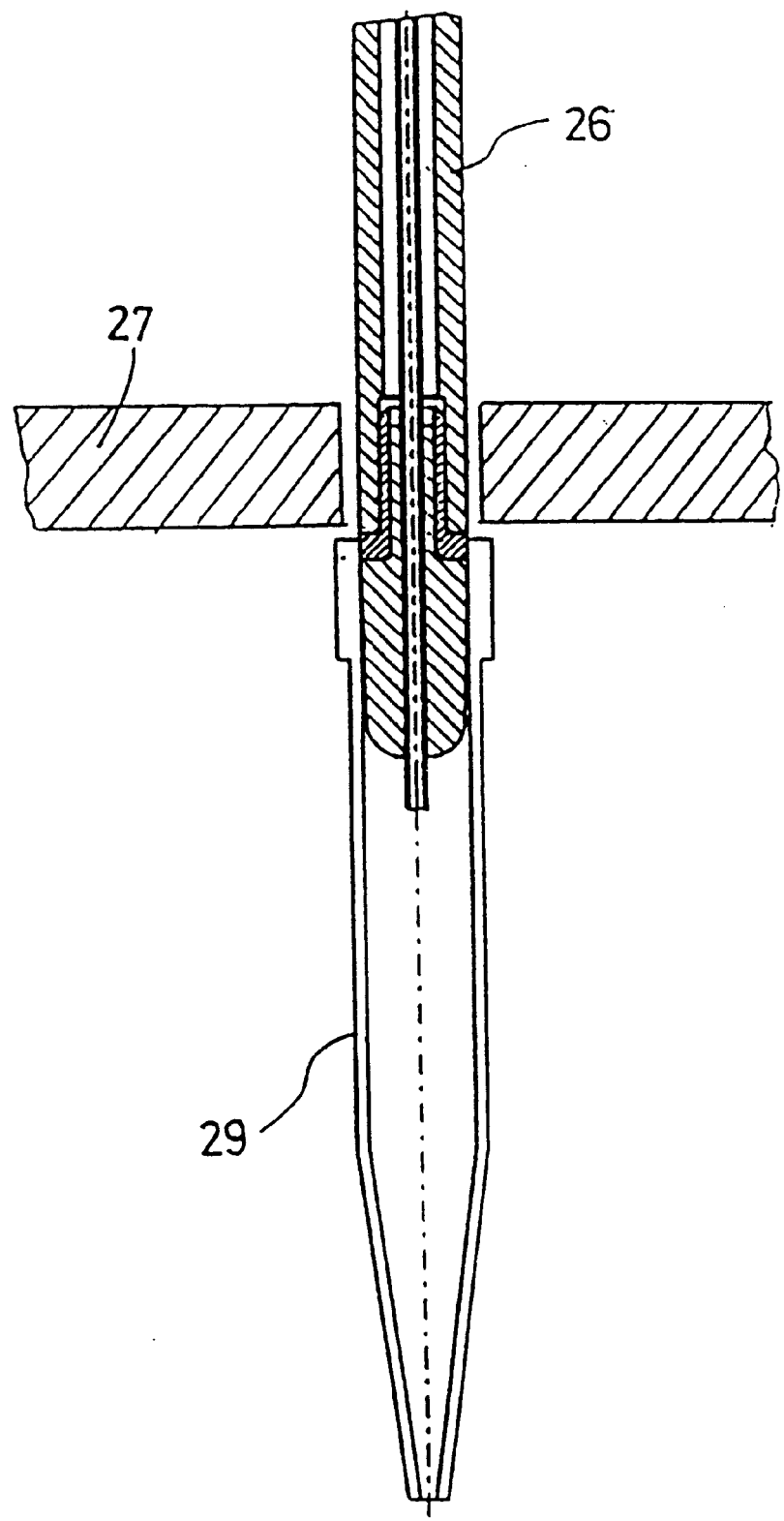
FIG. 6.1

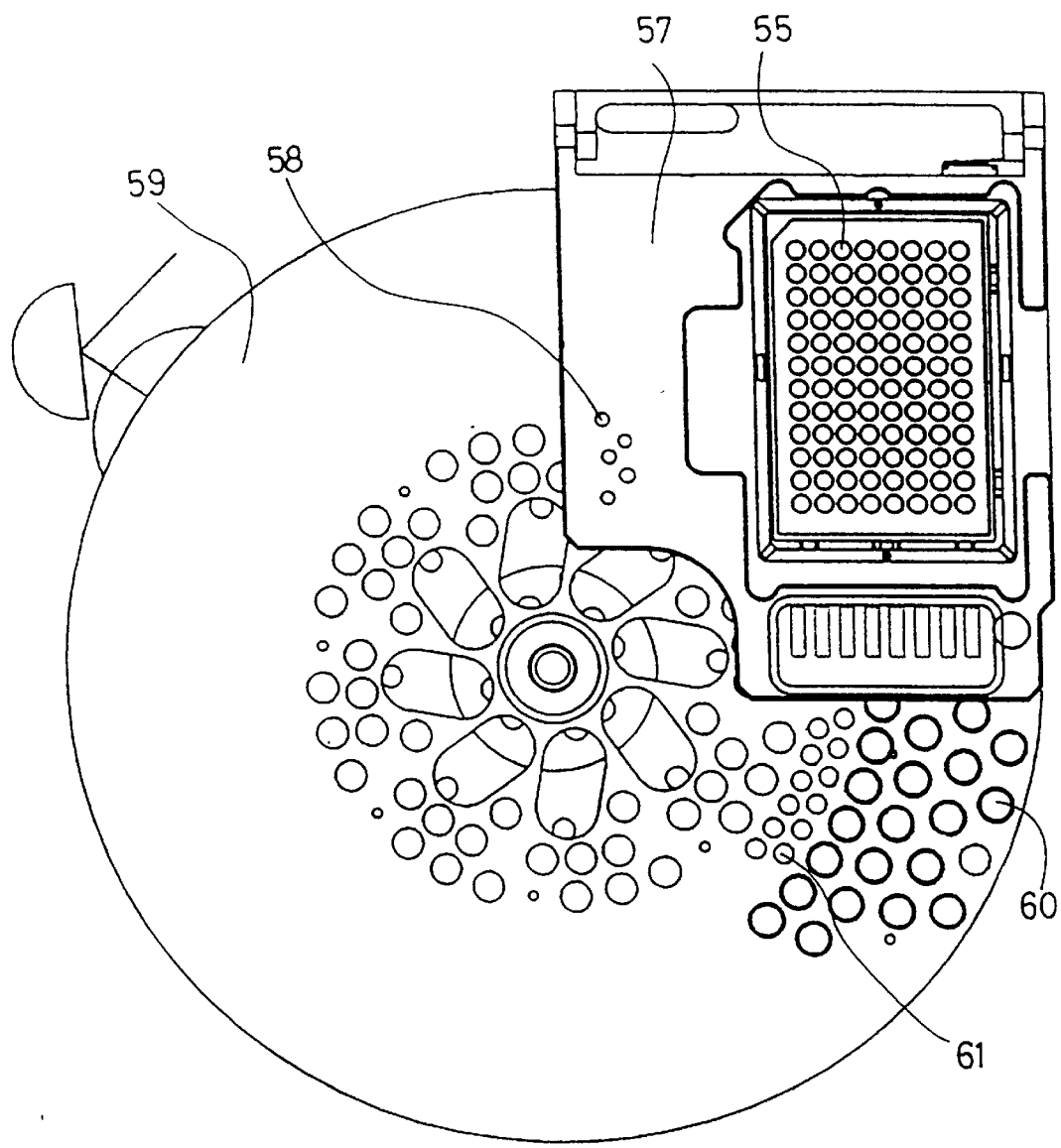
FIG. 12.1

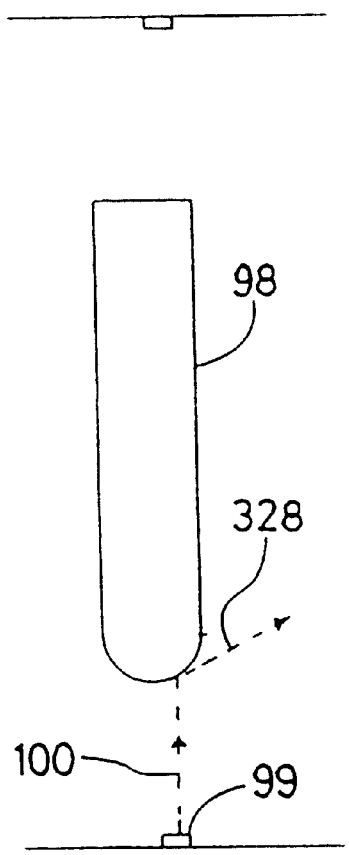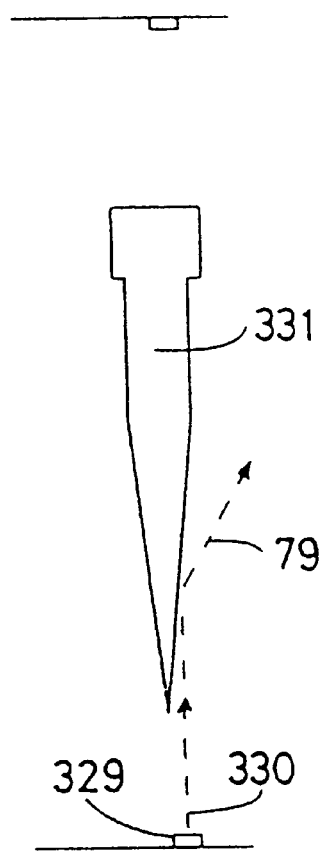
FIG. 13        FIG. 13.1

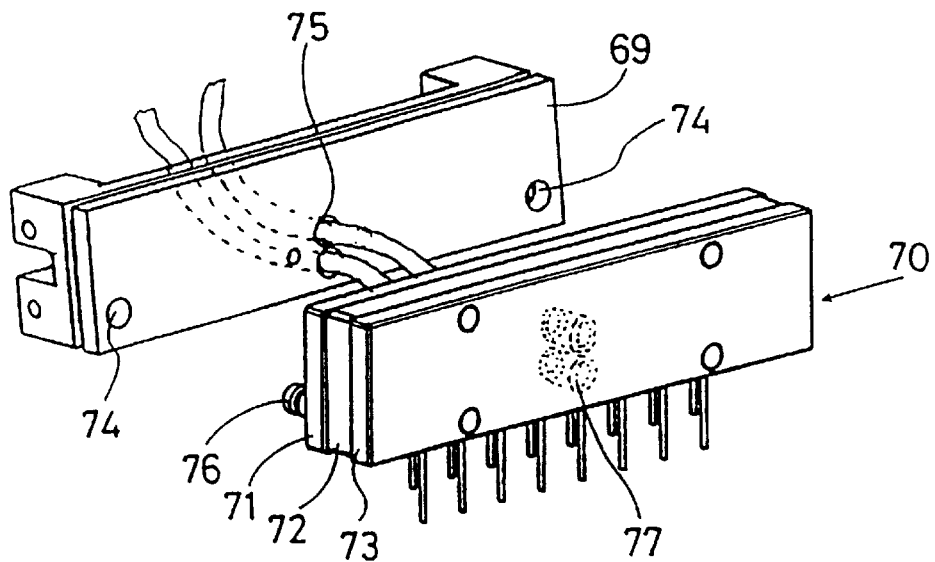
FIG. 15
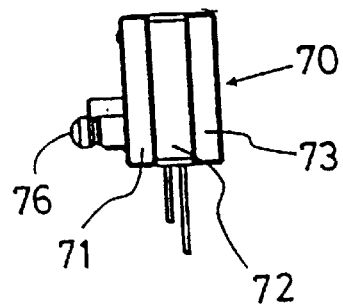
FIG. 15.1
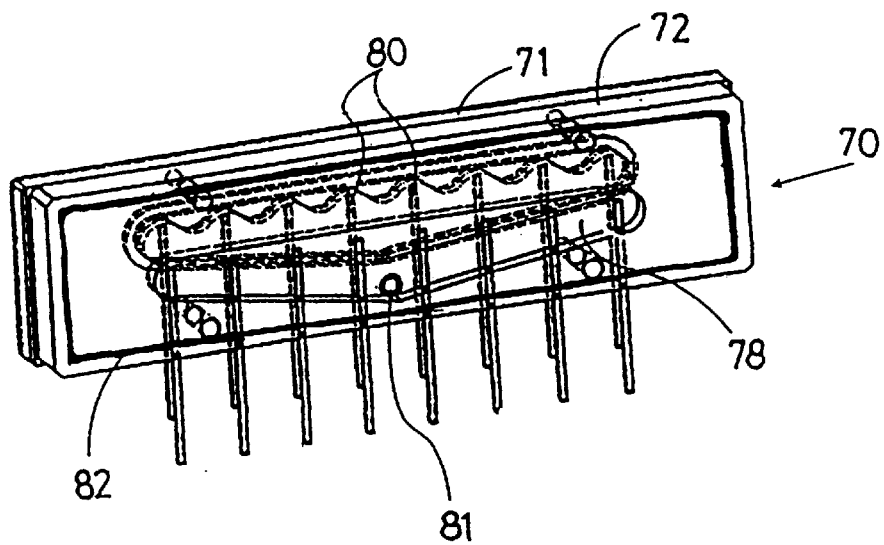
FIG. 16

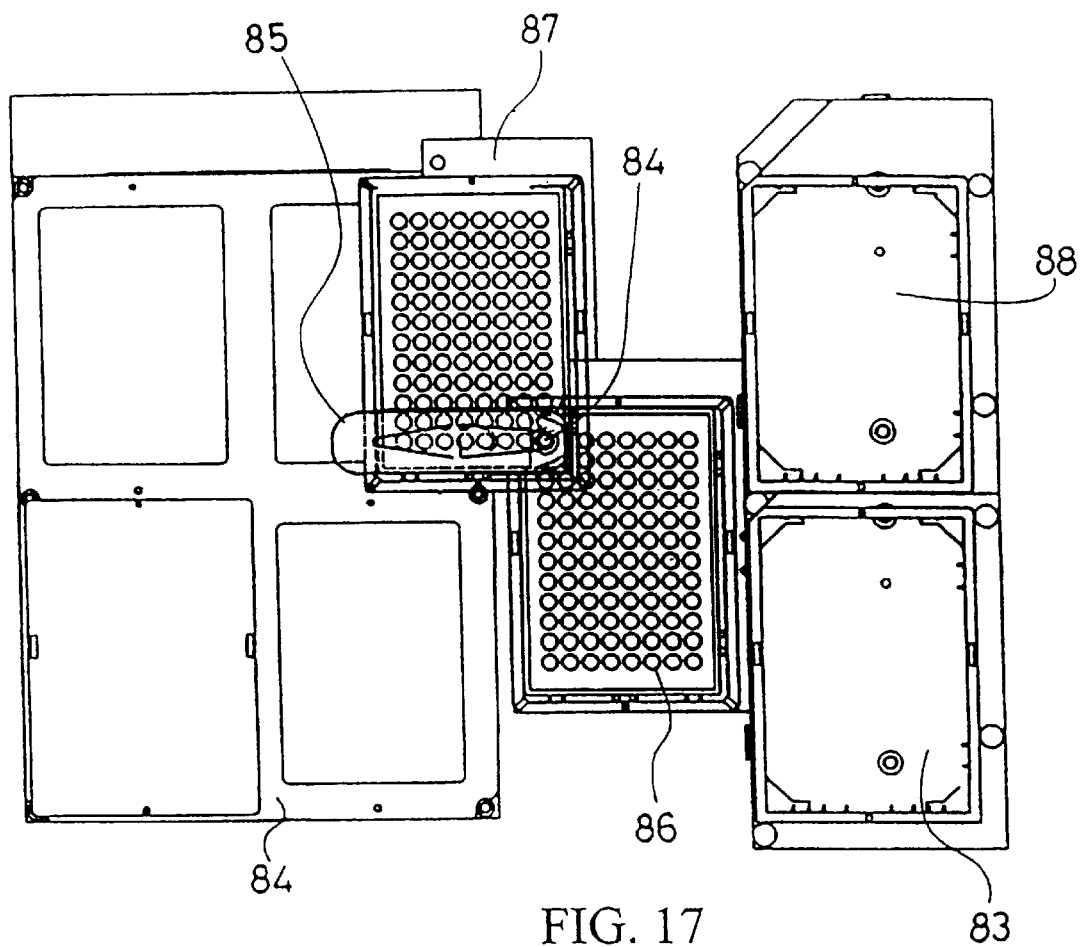
FIG. 17
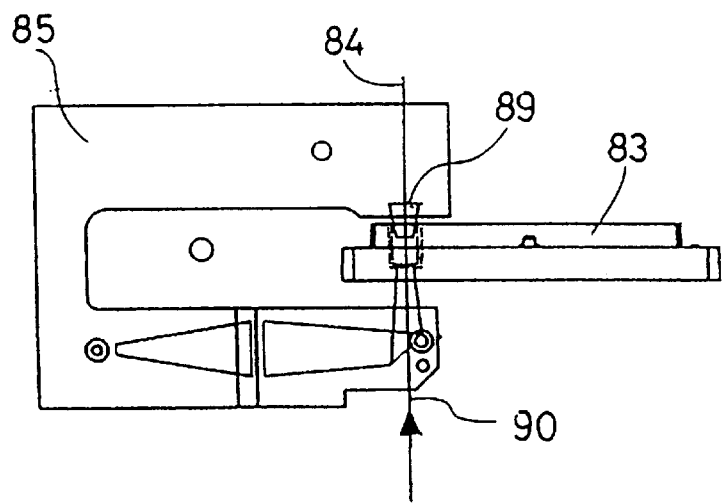
FIG. 17.1

APPARATUS FOR PERFORMING LABORATORY TESTS AUTOMATICALLY

FIELD OF THE INVENTION

The present invention is intended to disclose novel apparatus for performing tests on samples in a laboratory and, in particular, tests of the type known as ELISA.

BACKGROUND OF THE INVENTION

Automatic apparatus for performing tests known by the name of ELISA and similar tests perform the tests on supports having a plurality of cells or wells for facilitating parallel and orderly processing of the samples. These supports which are known as micro-titer plates, usually have a format of 8 by 12 wells and can sometimes be divided into strips of 8 or 12 wells which in turn can sometimes be divided into individual wells. These wells, which are moulded in plastics, usually carry a dried reagent bound to the walls or bottom in what is known as a solid phase. The various steps of the test are performed thereon and are generally:

1. Sampling and dilution of the samples, calibrations and checks on the wells of the plates. The dilutions require a specific diluent.
2. Incubation of the plate at controlled temperature with or without agitation for controlled periods of time (typically between 15 and 45 minutes, depending on the test).
3. Washing of the wells with a specific washing solution. This is usually performed by dosing the washing solution into the wells and subsequently emptying them.
4. Addition of various reagents (typically a specific, so-called conjugate test reagent, a chromogenic substrate, or a solution for stopping the chromogenic reaction).
5. Steps 2, 3 and 4 may be combined and repeated in various ways according to the type of test performed.
6. Photometric reading of the final reaction by various methods, one or several values being assigned to each cell.
7. Calculations, presentation and storage of the results corresponding to each sample.

It is important to keep the incubation times approximately equal for all of the wells so that operations which take place cell by cell and not with the whole plate at the same time must be performed within a relatively short time.

Although the micro-titer plates are similar to one another, they have slight differences, particularly in their external shape and size, which complicates their handling when an undifferentiated use of any type is required.

However, all currently-known apparatus for performing laboratory tests of the ELISA type have the disadvantage of poor efficiency in performing the tests, particularly owing to the need to perform a complete test on a certain sample-holder plate before the machine can receive further plates of samples in order to perform further sets of tests.

SUMMARY OF THE INVENTION

The present invention is intended to solve these problems, its main object being that the apparatus should work more efficiently with minimal dead times and with a capability for the apparatus to start further analysis tasks whilst the tasks in progress are being completed, the processing of new series of tasks being able to start even when the previous ones are not completed.

To achieve its objects, the present invention provides for the production of apparatus for performing automatic tests on samples for ELISA tests such that the loading of work series can take place separately from the processing thereof, means being provided for enabling predictions of time sequences to be known in real time in order to determine the moment at which new operations can start.

The invention provides for the apparatus to be constituted by two functionally separate, although intimately connected, regions of which the first, which permits interactive access by the user, permits loading of the samples, controls, calibrators, diluents and equipment necessary for performing the sampling and the dilutions, the plates on which the tests are performed being placed in the same region. The apparatus then performs the operations relating to the sampling and dilutions of the samples, checks and calibrations on the plate and transports the plate to the second separate region in which the rest of the operations are performed, the first region being left free for the loading of further series. The user can have occasional access to this second separate region of the apparatus in which the various stations dedicated to operations such as incubation, washing, reading, etc. are situated. Several different plates at different stages of the process may be in the second region at the same time. The apparatus has means for moving the plates from one station to another as required by the process until the operations to be performed have been completed. Finally, the apparatus deposits the plates in an output station as each plate completes the process allotted thereto.

Within the logical limitations of compatibility between tests, number of reagents, etc., the system has optimal characteristics for working in accordance with concepts which may be called multi-parameter working and multi-series working. The term multi-parameter working is intended to define in this description the performance of several tests at the same time on a set of samples on one or several separate plates. The concept of multi-series working is intended to define in this description a capability to start new series of tasks with the same or different sets of tests and with the same or different sets of samples, even when the previous ones have not been completed.

The appropriate configuration of the apparatus comprises a robotized arm for moving in accordance with X and Y coordinates over the two above-mentioned regions and also for moving along an axis perpendicular to the plane of the former coordinates, that is, a Z axis, by means of a device for performing various functions of movement, level-detection and ejection or recovery of elements necessary for the analysis.

For locating the micro-titer plates etc., the present invention provides for the use of a special frame for the arrangement of micro-titer plates of any type with anchorages and locating elements suitable for automation thereof.

The movements along the Z axis are brought about by means of a movable carriage or "Z tower" which has a special gripper or claw provided with locating elements similar to those of the frames and their lids, for performing the transportation.

Within its general structure, the apparatus comprises, in a first region, a carousel for the positioning of the samples, the reagents and equipment necessary for the sampling and dilution of the samples, with a platform which can be lowered for housing a plate or a number of superimposed plates with the wells for the test to be performed. A reader for reading the bar codes of the samples and a system for rotating tubes to facilitate the reading of their bar-codes are also located in the first region.

The so-called Z tower or vertical movement carriage has two independently vertically movable probes and a vertically movable gripper or claw for gripping by means of movable hooks.

The incubation, plate-washing, reading, lid-storage, and plate-storage stations, a station for storage and output of the plates, a tray for reagents and disposable level-detection tips, as well as other elements connected therewith are disposed in the second region of the apparatus which is generally arranged in a side portion of the main table thereof.

BRIEF DESCRIPTION OF THE DRAWINGS

For a better understanding, some drawings of a preferred embodiment of apparatus according to the present invention are appended by way of non-limiting example.

FIG. 2 is a perspective view of a special frame for carrying the micro-titer plates.

FIG. 2.1 is a detail showing the frame of FIG. 2 in perspective.

FIG. 2.2 shows a lid for closing the frame shown in FIG. 2.

FIGS. 2.3 and 2.4 show respective details in section.

FIG. 3 is a perspective view of the gripper or claw of the vertical carriage or Z tower.

FIG. 3.1 is a side elevational view showing schematically the gripper of FIG. 3.

FIG. 6.1 is a schematic section through a syringe with a disposable tip.

FIG. 12.1 is a plan view of the disk of FIG. 12 showing the position of a micro-titer plate.

FIG. 13 shows the relative positions of a sample tube and a light beam for detecting the presence thereof.

FIG. 13.1 is a view similar to FIG. 13 showing the same detector-beam arrangement for a disposable tip for a syringe.

FIG. 15 is a perspective view of the head of the washing unit of the apparatus with parts partially disassembled.

FIG. 15.1 is a side elevational view of the head of the washing device.

FIG. 16 shows a detail of the head of the washing device.

FIG. 17 is a simplified plan view in which the position of the plate for photometric determination can be appreciated.

FIG. 17.1 is a schematic side elevational view.

DESCRIPTION OF PREFERRED EMBODIMENTS

Figure 1:
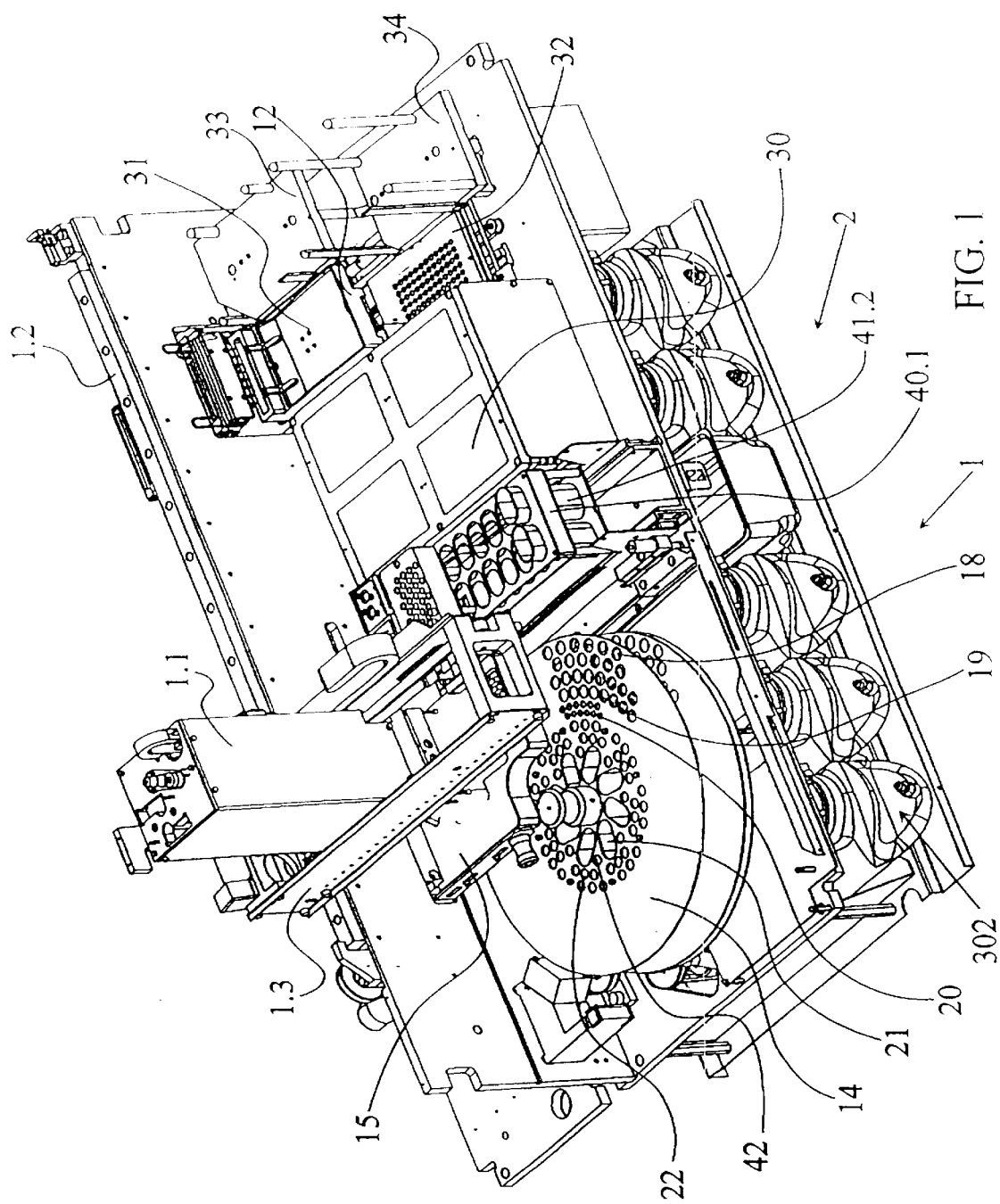
FIG. 1 is a simplified perspective view of the apparatus of the present invention.

As can be seen in the drawings, the members of the apparatus as a whole are arranged basically on a single table, of which two main sections 1 and 2 which can operate separately, can be appreciated, the former affording interactive access for the user and permitting the loading of the samples, controls, calibrators, eluents and equipment necessary for the sampling and dilutions. A carriage 1.1 in an upper arrangement is movable vertically along the Z axis and is also movable on guides 1.2 and 1.3 which define the X and Y coordinate axes so that the carriage 1.1 can reach any of the points both of the section 1 and of the section 2, performing the vertical movements necessary for carrying out the appropriate operations at each of the points in these regions. The plate on which the tests are performed is placed in the first region, the apparatus performing the operations relating to the sampling and dilution of the samples, controls and calibrators on the plate and transporting the plate, by means of the movable carriage 1. 1, to the region 2 in which the rest of the operations are performed, the region 1 being left free for the loading of a further series. The user can have access to the second region 2 occasionally. Within the region 2 there are various stations dedicated to operations such as incubation, washing, reading, etc. and several plates at different stages of processing may be therein at the same time. The movable carriage 1.1 moves the plates from the station 1 to the station 2 as necessary in order to complete all of the operations provided for and finally deposits them in an output station.

Figure 6:
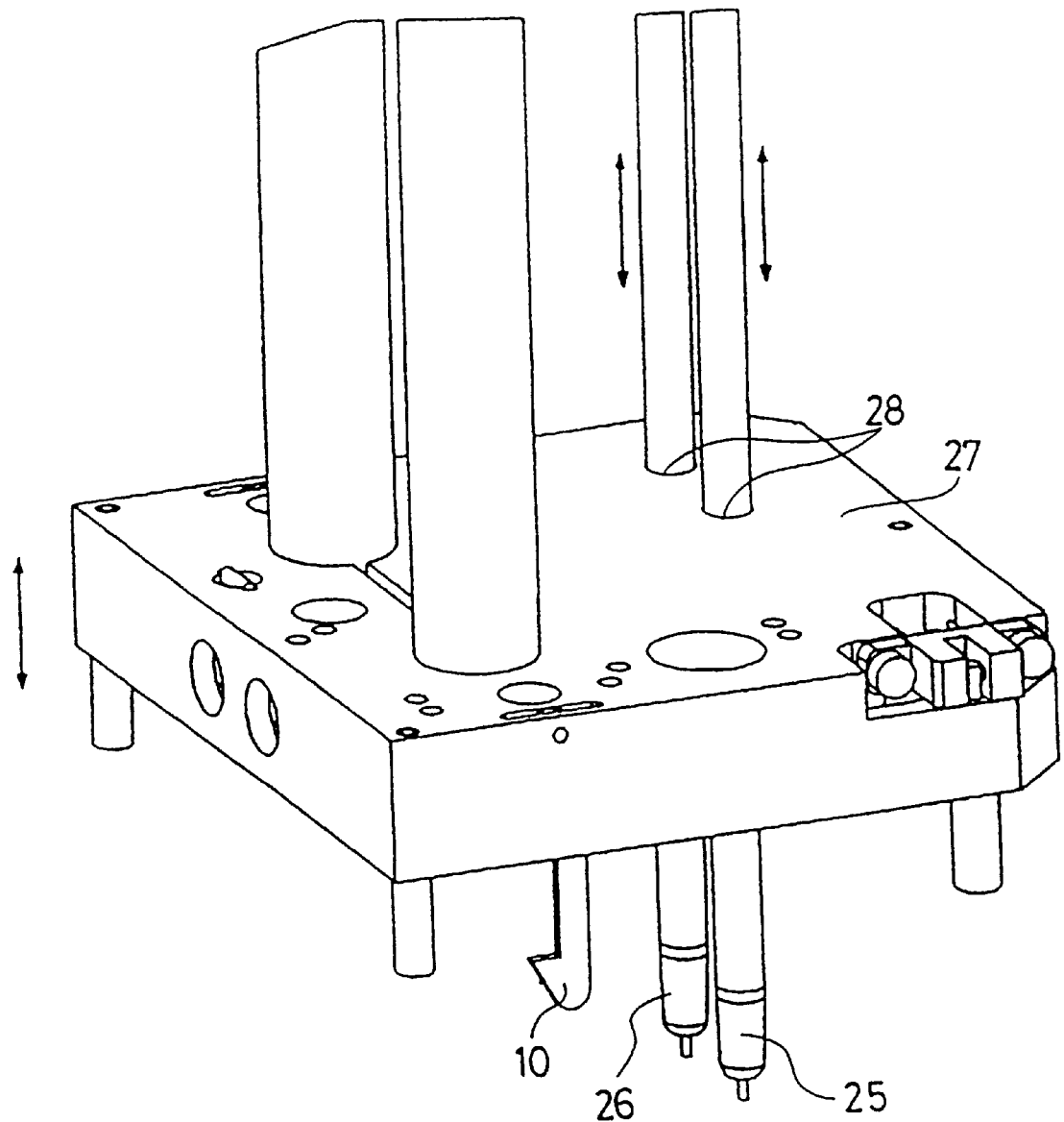
FIG. 6 is a schematic perspective view of the vertically movable carriage or Z carriage of the machine.

The movements of the movable carriage 1.1 are fully robotized and the carriage has means for the independent and controlled vertical movement of two probes by means of which the liquids are manipulated and which have a level detector device which can operate directly or with disposable tips, indicated 29, as shown in FIG. 6.1. The carriage can also bring about vertical movement of a third element 27 which incorporates the claw, FIG. 6, in order to grasp the raised plates and enable them to be translated thus positioned, and finally to release them.

On account of the differences between the micro-titer plates, the present invention provides for the production of a special frame 3, see FIG. 2, which can house micro-titer plates of any type without distinction, since it has anchorages 5 of various sizes and shapes and locating elements 6 suitable for enabling the frame to be handled safely. These frames are stackable, improving the logistics of the apparatus. In order to render the temperature of the plate uniform and to prevent evaporation of its contents, the present invention provides for special lids 4 which can be coupled with the frames so that the micro-titer plate is covered. The lids have anchorages of similar size and shape to those of the frames 3 and are also stackable. The anchorages are constituted by slots 5.1 with an internal recess 7. The locating elements are complementary small cylindrical stacking projections, indicated 6.1, which fit in the cavities 8 and 8.1 to permit stacking (FIGS. 2,2.1,2.2,2.3 and 2.4).

The lower end of the vertically movable tower or carriage 1.1, FIG. 3.1, has a vertically-movable gripper or claw plate 9 which has locating elements 11 similar to those of the frames 3 and the lids 4 and pivotable hooks 10 which can enter the slots 5 and 5.1 in order to grasp the frame 3, the corresponding plate or the lid 4 for transportation. The hooks 10 form a pair and are associated with an intermediate connecting bridge 10.1 which allows them to pivot as shown by the arrow 10.2.

Figure 4:
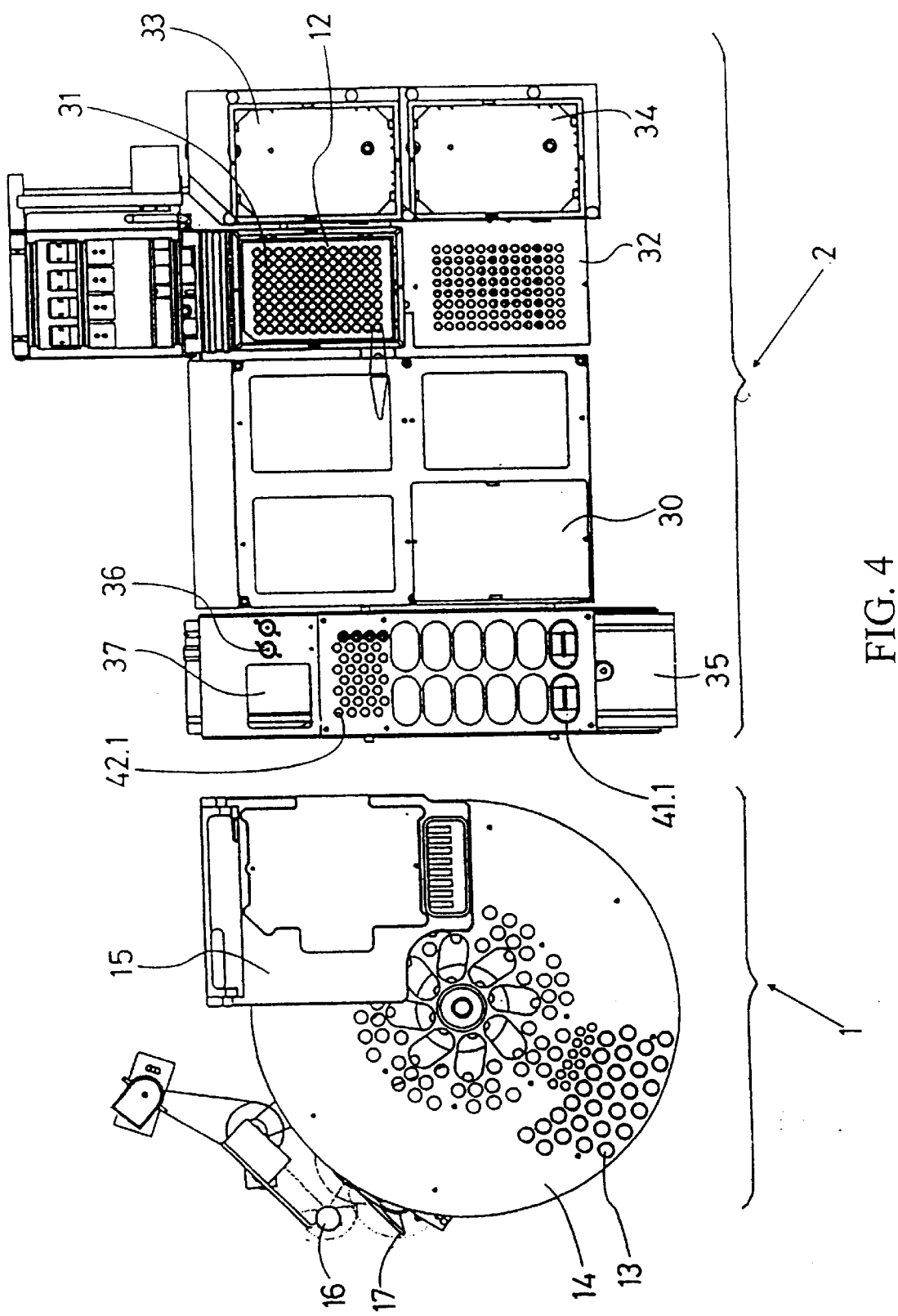
FIG. 4 shows schematically a top view of the members of the apparatus as a whole, disposed on the table carrying them.

The general configuration of the apparatus can be appreciated from FIG. 4 which shows, in the first region, on the left-hand side, a carousel 14 on which the samples, the reagents and the equipment necessary for the sampling and dilution of the samples are disposed, and which also has a platform 15 which can be lowered and which can house a plate with the corresponding frame in which the required number of wells suitable for the test or tests to be formed are disposed. The vertical carriage 1.1 moves above the region I in order to perform the sampling and dilutions by means of the two probes, above the micro-titration or micro-titer plate disposed on the platform 15. Once this stage is completed, the claw 9 of the vertical carriage 1.1 grasps the plate with its frame and transports it to the second region 2 of the apparatus, the rest of the processes being performed within the second region, thus allowing the user to prepare a new series in the first region.

The first region I carries, in addition to the elements indicated, a reader 16 for reading the bar-codes of the samples and a system for rotating the tubes 13 disposed on the carousel 14 in order to locate the bar code of the sample tube so that it faces the bar-code reader 16, the tube-rotating device being generally indicated 17 in FIG. 4.

Figure 5:
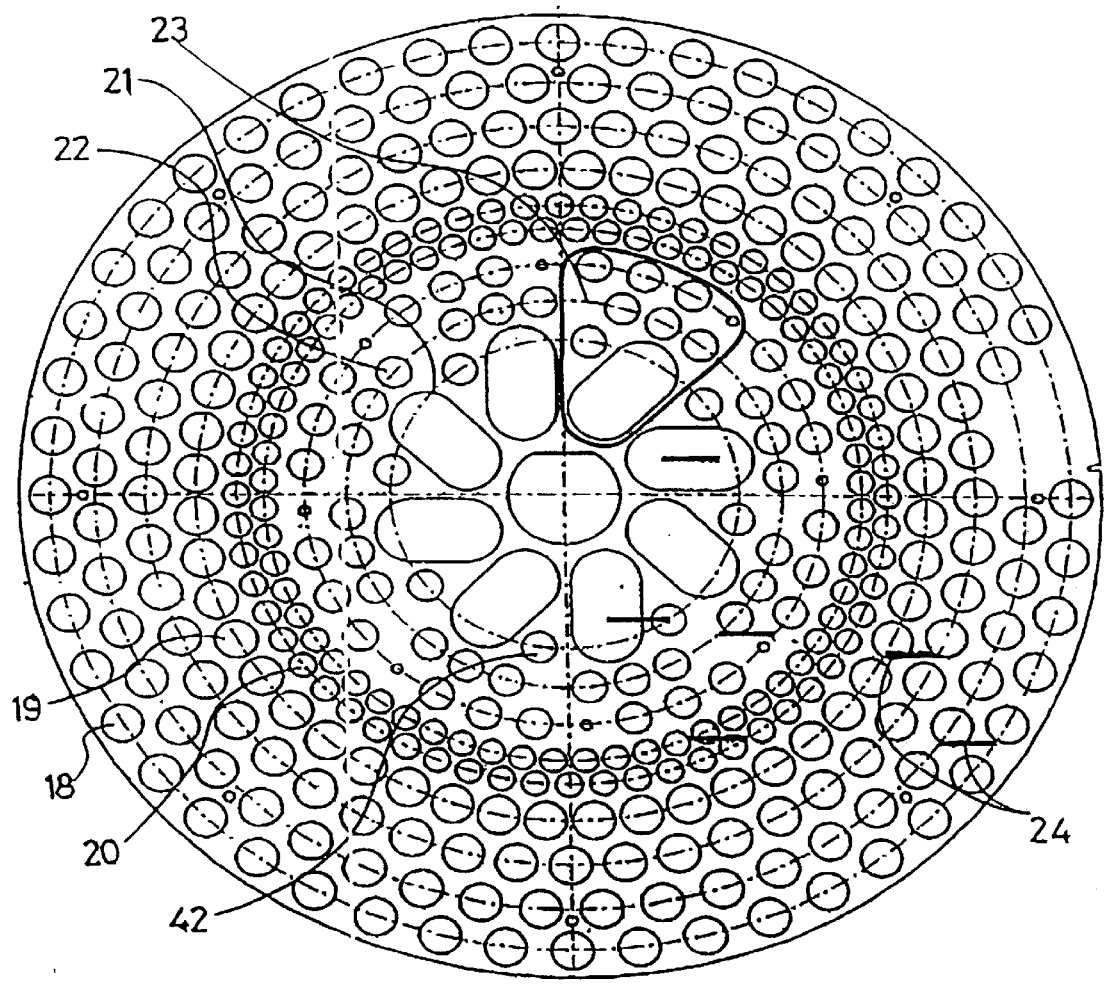
FIG. 5 is a schematic plan view of the rotatable disk or carousel of the apparatus.

FIG. 5 shows a detail of the configuration of the carousel in which sample tubes 18, tubes 19 for forming pre-dilutions if necessary, and housings 20 for the disposable tips necessary for the sampling operations and dilutions can be seen. The carousel comprises eight sectors, one of which is indicated 23, there being space in each sector for seven calibrators and controls indicated 22, and for diluent, indicated 21. Each sector corresponds to a possible test to be performed in the same series, so that the multi-parameter concept explained above represents a maximum of eight tests.

The specific arrangement of the housings enables the two probes to be used in a manner such that they can have access to one of the following pairs at a time.

2 samples
2 disposable tips
2 pre-dilution tubes
2 calibrators or controls
1 calibrator and diluent, or
the two probes in the same diluent.

The pairs mentioned, which are 18 mm apart, are shown joined by the lines indicated 24 in FIG. 4. The distance between the probes is such that dispensing can take place into the micro-titer plate, into pairs of wells separated by one cell (the normal distance between the wells of the micro-titer plate is 9 mm). Clearly, this optimizes execution times since the probes can work at the same time without loss of the ability of any syringe to operate independently of the others should the need for this be determined by the algorithm within the apparatus.

FIG. 6 shows schematically the movable portion of the vertical displacement head 1.1. This drawing shows the two independently vertically movable probes 25 and 26 and the claw 27 which is also capable of its own vertical movement and engagement by means of the movable hooks 10. It can be seen that the probes extend through the claw 27, through holes 28. If disposable tips 29 are used, FIG. 6.1, these have a larger diameter than the holes 28 so that a combined movement of the probes and the claw ejects the disposable tip.

In the second region of the instrument there is a series of elements which, by way of non-limiting example, may comprise, see FIG. 4: four incubation/agitation stations 30, a plate-washing station 31, a reading station 32, a lid-storage station 33, a station 34 for the storage/output of processed plates, a tray 35 for reagents and disposable tips, an opening 37 for the ejection of disposable tips, and a syringe-tip washing station 36.

When the sampling and dilution of a plate has been completed, the plate is transported to one of the four incubators and a lid is placed thereon. From this moment, the vertical carriage or Z tower 1.1 manipulates the various lids and plates being processed in a manner such that they are in the various locations necessary for the process, such as the washing station, the incubator station, the reader station, etc., at the required times. The vertical carriage 1.1 also dispenses the various reagents required, which are located on the reagent tray 35, by means of the two probes (with or without disposable tips).

The microprocessor of the apparatus continuously calculates a forecast of tasks and sequences of operations by means of the appropriate algorithm so as to fulfill the requirements for each test, permitting the entry of a new series provided that the time lags provided for each operation, which fit the requirements of the new series or can be made to fit by fine readjustments compatible with the series in progress, are left free.

The apparatus comprises a further series of elements necessary for its operation as a whole, which are not shown in detail for greater clarity of illustration; these are, for example: precision digital pumps for aspiration and dosing by means of the probes; a fluid system which permits the use of four different plate-washing solutions depending on the test, priming, washing and rinsing of the system itself and disposal of liquids, electronic and mechanical systems necessary for performing all of the functions indicated, and an external computer with a data-input program, a system for interaction with the user, process computation, process control, computation of results, data storage, statistical calculations, presentation of results, and procedures for bidirectional communication of data with other systems.

A system of reservoirs for washing and waste solutions, integrated in the lower portion of the main table of the apparatus, is also not shown for greater clarity.

Figure 7:
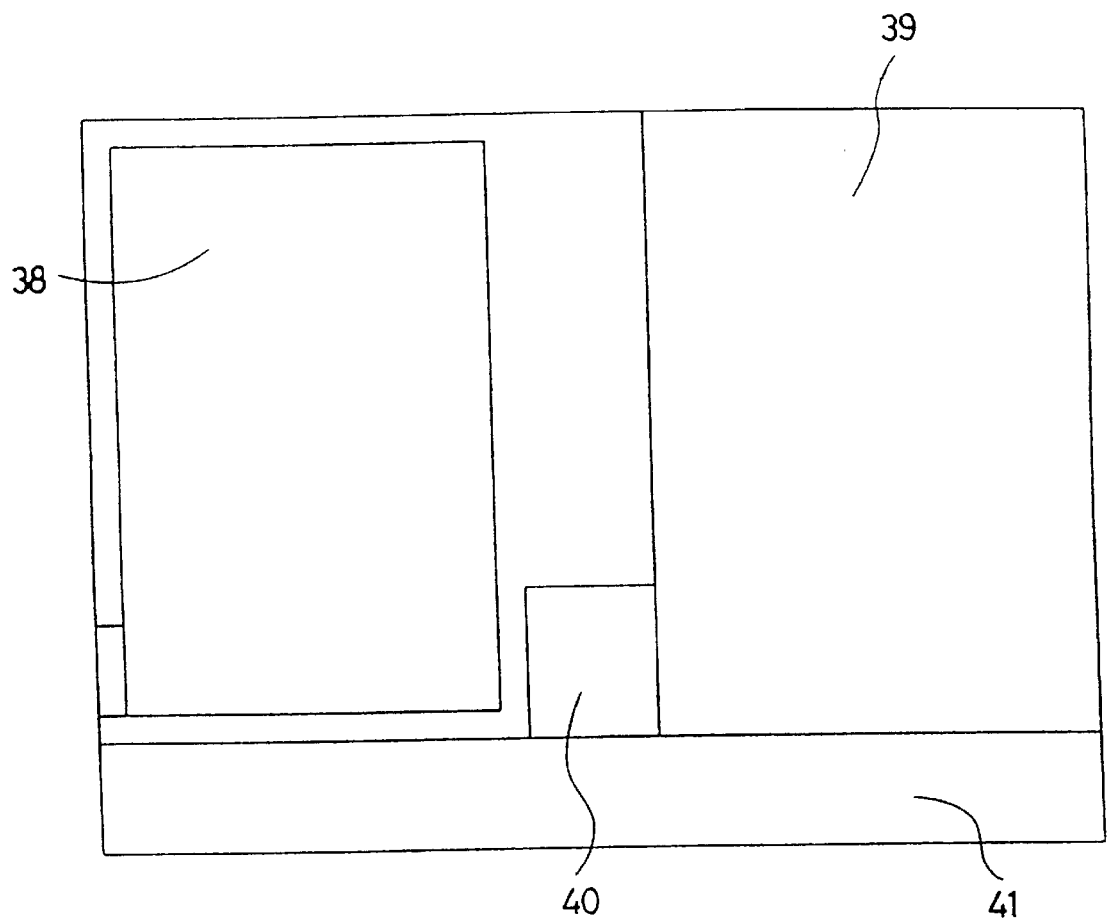
FIG. 7 is a schematic plan view of the system of covers for closing the apparatus at the top.

The present invention provides for the members of the machine as a whole to be completely enclosed or protected as shown schematically in FIG. 7, which shows various separately operable closure elements, such as an access door 38, a lid 40 for the reagent tray 40.1, FIG. 1, a door 39 for access to the plate-processing and disposal area, as well as a door 41 which can be lowered for access to the reservoirs of washing and waste solutions and used-tips disposal bin.

The carousel can be removed so that it is possible to have two carousels in order to be able to prepare one whilst the other is processing. The access door 38 slides into the apparatus so that, when it is opened, it is interposed between the two areas of the apparatus, thus enabling loading to be performed without risk to the user. The doors 38 and 40 can operate only when the process permits, for which purpose they have safety locks. The access 41 is clear in order not to affect safety and the access 39 automatically de-activates any movement inside the apparatus.

A device with optical detectors enables the presence of sample tubes, dilutions, disposable tips and controls, calibrators and diluents in the carousel to be checked. Moreover, optical detectors of the plate-loading region enable the presence of the removable wells in the plate to be checked. This permits checking of the preparation of a test which prevents errors or problems arising in the correct operation of the apparatus.

Figure 12:
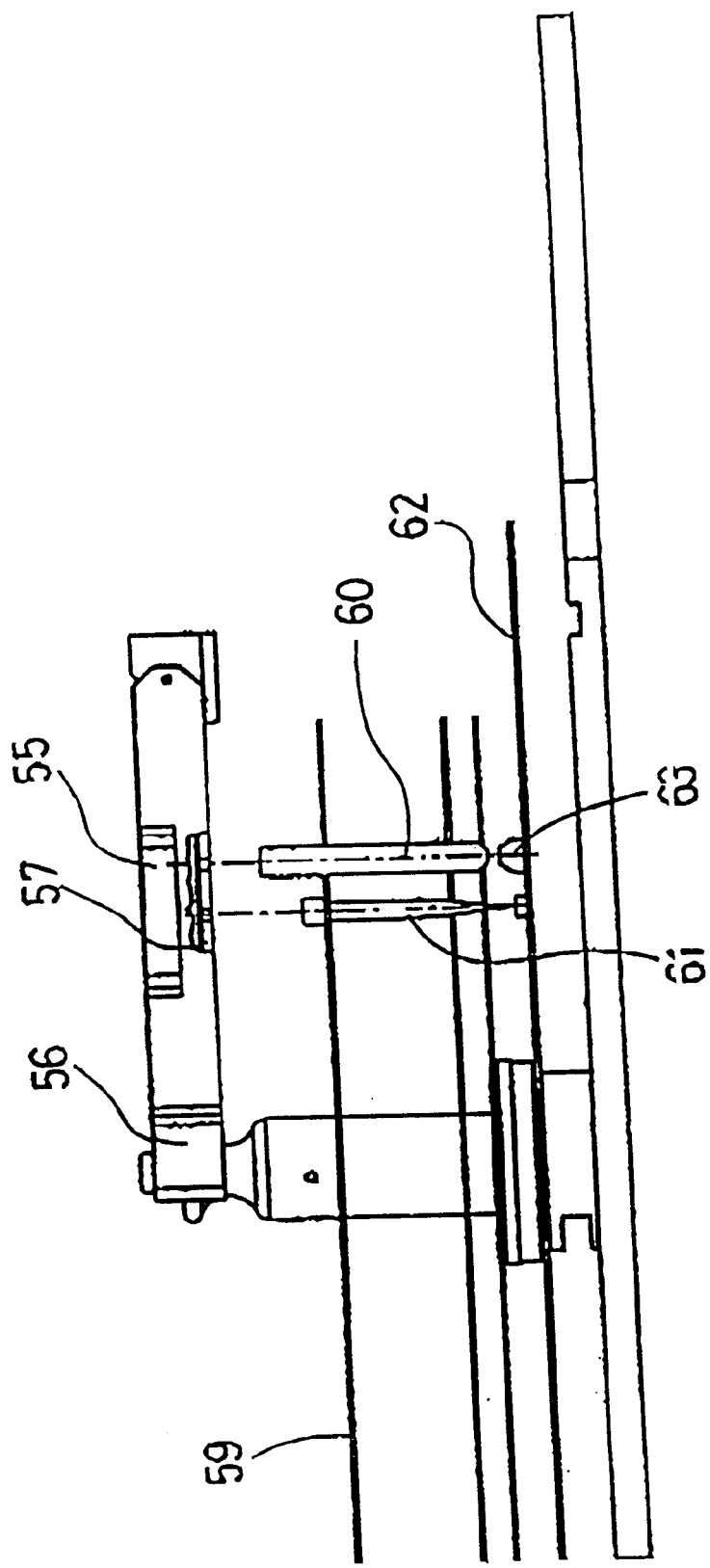
FIG. 12 is a side elevational view of the rotatable disk or carousel of the apparatus.

Some of the detectors are reflection detectors and others are transmission detectors. A plan view of the carousel and plate-loading region can be seen in FIG. 12.1 and a elevational view thereof can be seen in FIG. 12. The plates are disposed on the support 55. A set of eight reflection detectors arranged in line is indicated 56. When there is a new plate on the support 55, the transportation system picks it up and passes it over the region 56, placing each row of wells facing the eight sensors, checking the presence of the wells of the plate.

The detectors indicated are mounted on the plate 57 which also contains a set of light detectors 58 corresponding to different concentric alignments of the carousel 59, such as sample tubes 60, disposable tips, 61, etc.

Underneath the carousel there is a second circuit 62 with light emitters 63 which correspond to the above-mentioned detectors 58. When an element such as a tube or a disposable or non-disposable tip etc. is present, the light beam between the emitter and the receiver is interrupted. According to the present invention, this system is preferable to the location of reflection detectors in a lower position. To achieve optimal operation, the light beam is placed slightly out of alignment with the central axis of the element, as shown in FIGS. 13 and 13.1, so that the tubes deflect the light beam, since, as some tubes are transparent, they do not block the light beam and, in the case of disposable tips such as 29, so that the beam is also prevented from passing through the end hole. In FIG. 13, in which a sample tube is indicated 98 and, in the lower portion, the light emitter is indicated 99, it can be seen that the beam 100, which is out of centre relative to the axis of the tube 98, departs laterally out of centre in the form of the reflected beam 328. In the case of FIG. 13.1, a similar arrangement is shown with a lower emitter 329 such that the beam 330 is out of centre relative to the disposable tip 331, being reflected sideways in the form of the light beam 79.

Other elements of the carousel are detected by reflection detectors mounted on the plate 62.

For diluents and reagents, the present invention provides for special containers, indicated 21 and 41.1 in FIGS. 5 and 4, respectively. In the carousel, it is also possible for the probes to be input in parallel, one to the diluent and the other to a calibrator indicated 42 in FIG. 5. This takes place because many techniques use the same diluent as a "white" or reference calibrator.

Figure 8:
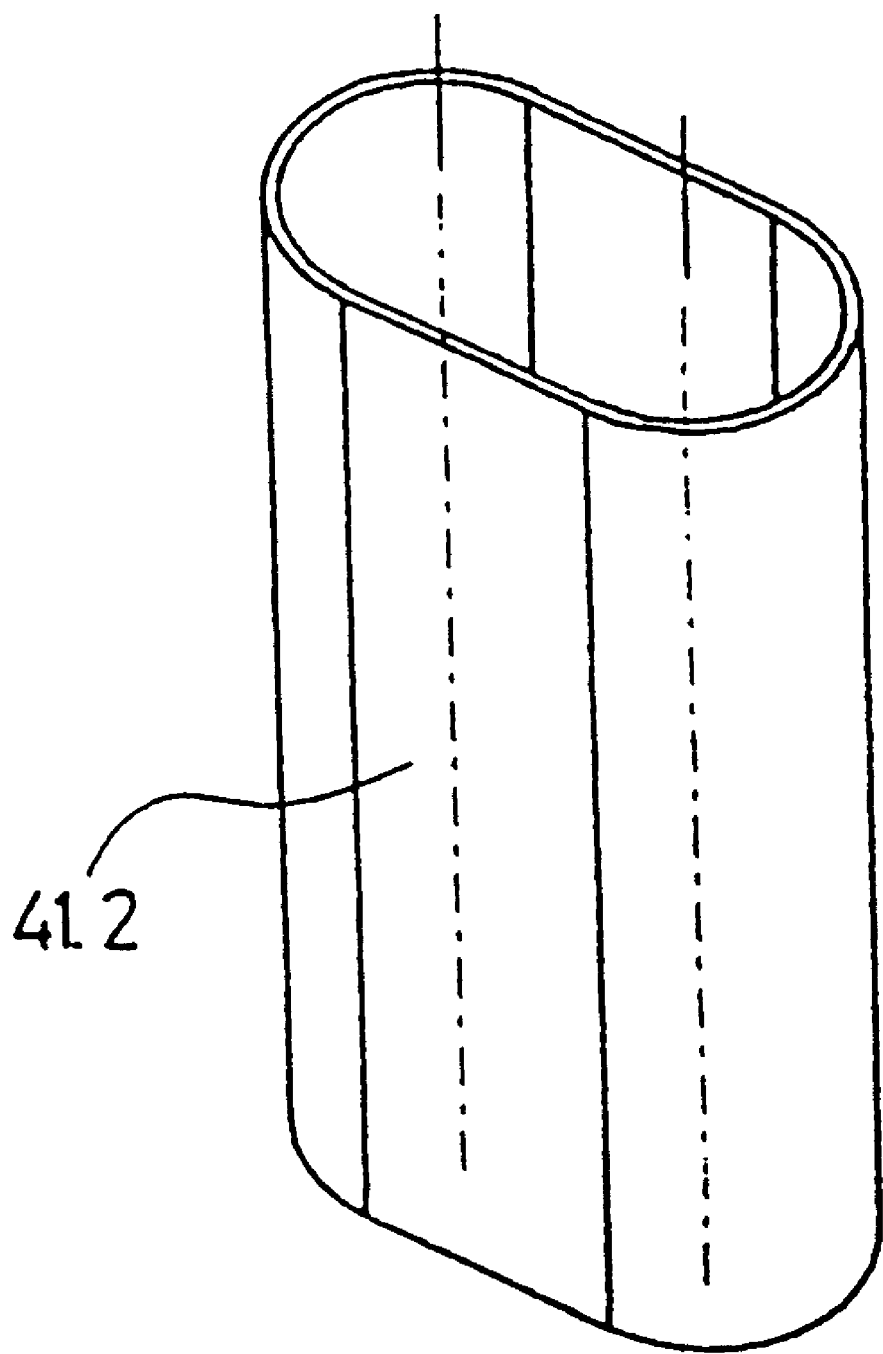
FIG. 8 shows a special container for diluents for use with the apparatus of the invention.

The reagent tray 35 has space for a plurality of containers such as those indicated 41.2 in FIG. 8 and a region 42.1 for a quantity of disposable tips which is at least twice the quantity of containers so that there is at least one per syringe and per reagent. The disposable tips can be re-used within the same work session for reagents which do not change.

The tips for sampling are in the carousel and those for processing are on the reagent tray so that interference between the various operations is minimal.

Figure 9:
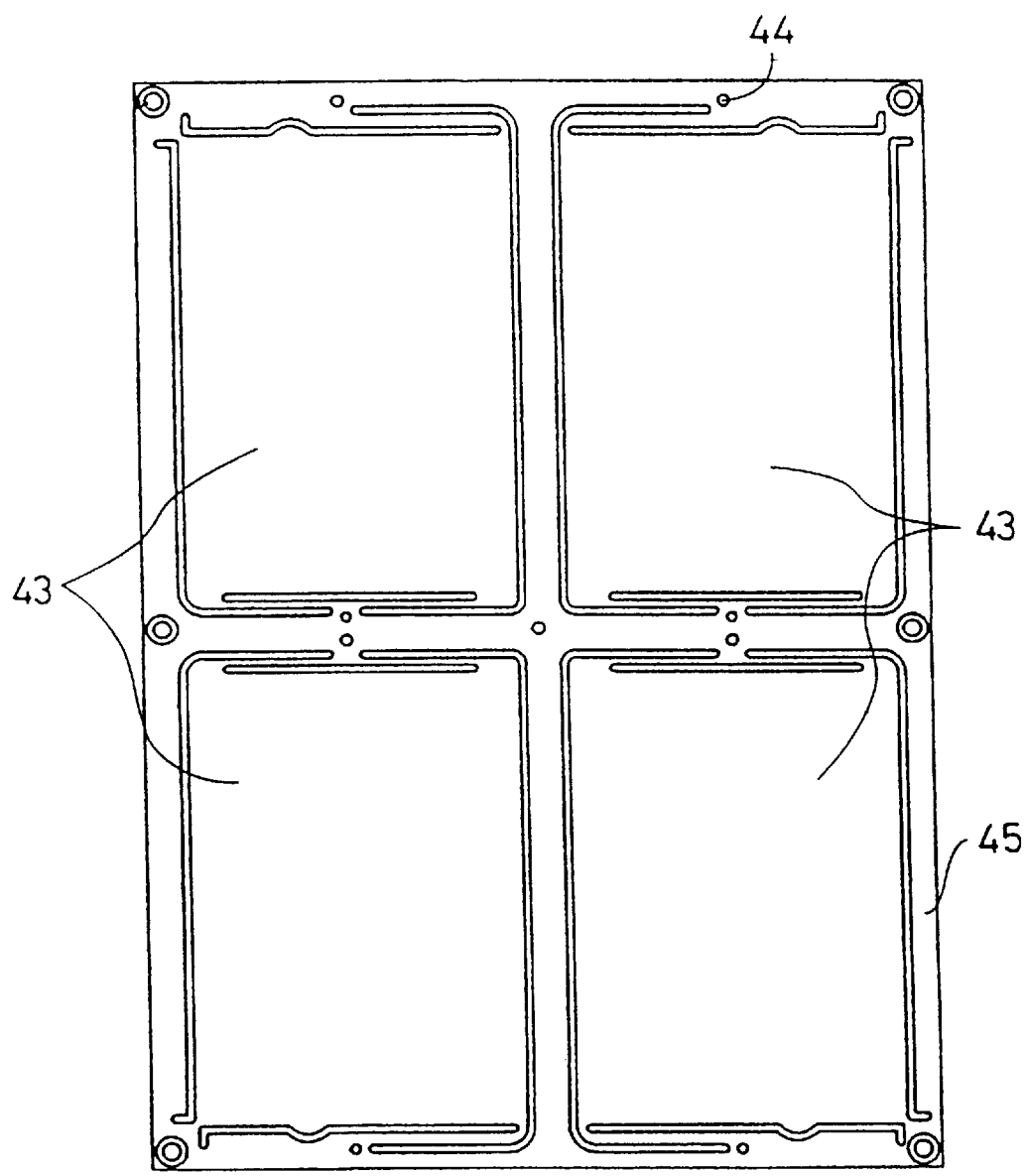
FIG. 9 is a plan view of a base with differentiated heating for supporting the micro-titer plates.
Figure 10:
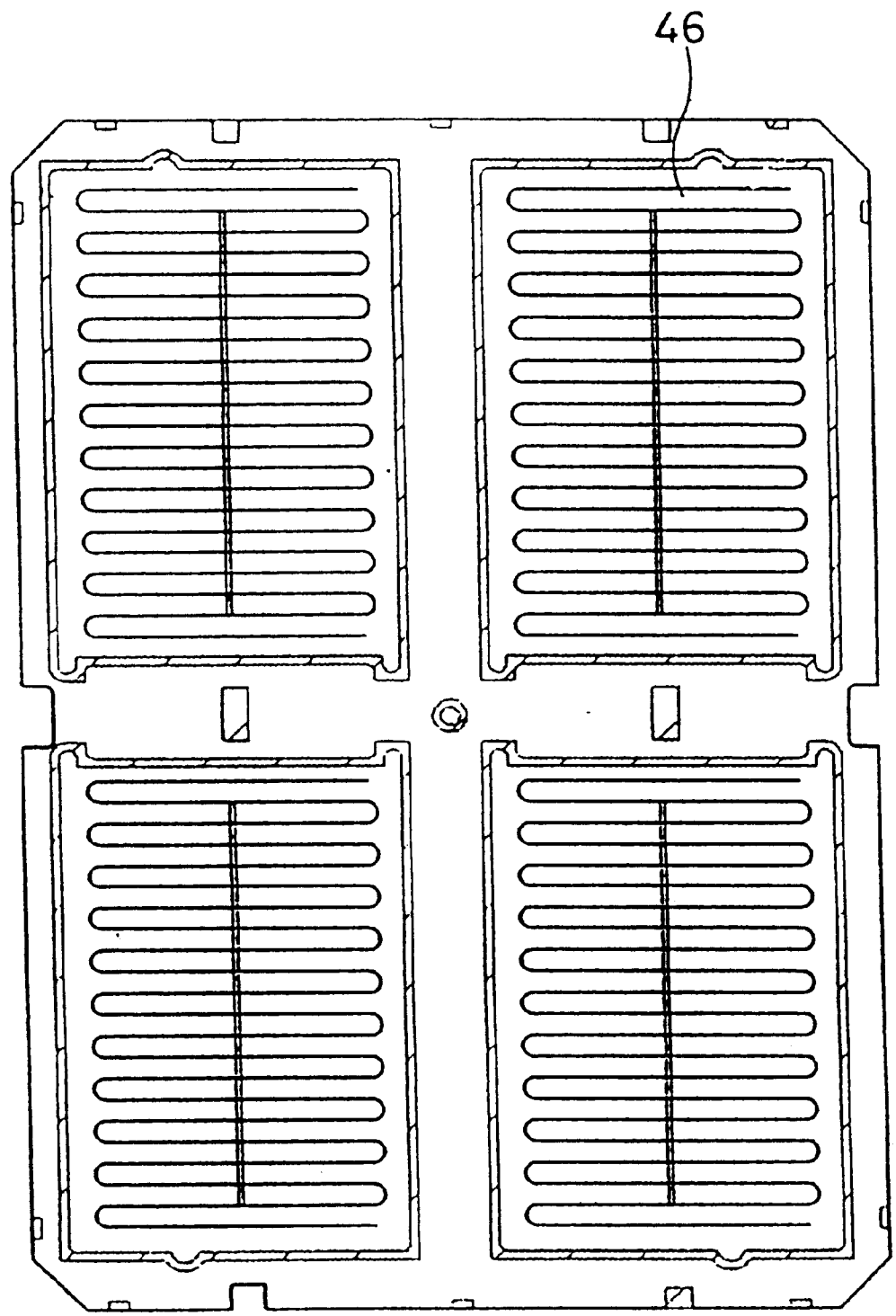
FIG. 10 shows schematically the arrangement of means for the individualized heating of the plate of FIG. 9.

FIG. 9 shows an aluminum plate 45 with perforations which define four independent regions 43 each of which is heated independently to a predetermined temperature, normally between room temperature and 60° C., typically 37° C. The labyrinthine paths between one region 43 and another adjacent region ensure that there is little transmission of heat so that there is little influence of one region on another. An adhesive sheet is placed on the plate so obtain a leakproof surface.

Each of the regions has two locating elements 44 so that frames 3 or lids 4 of the type described above can be placed thereon.

Figure 11:
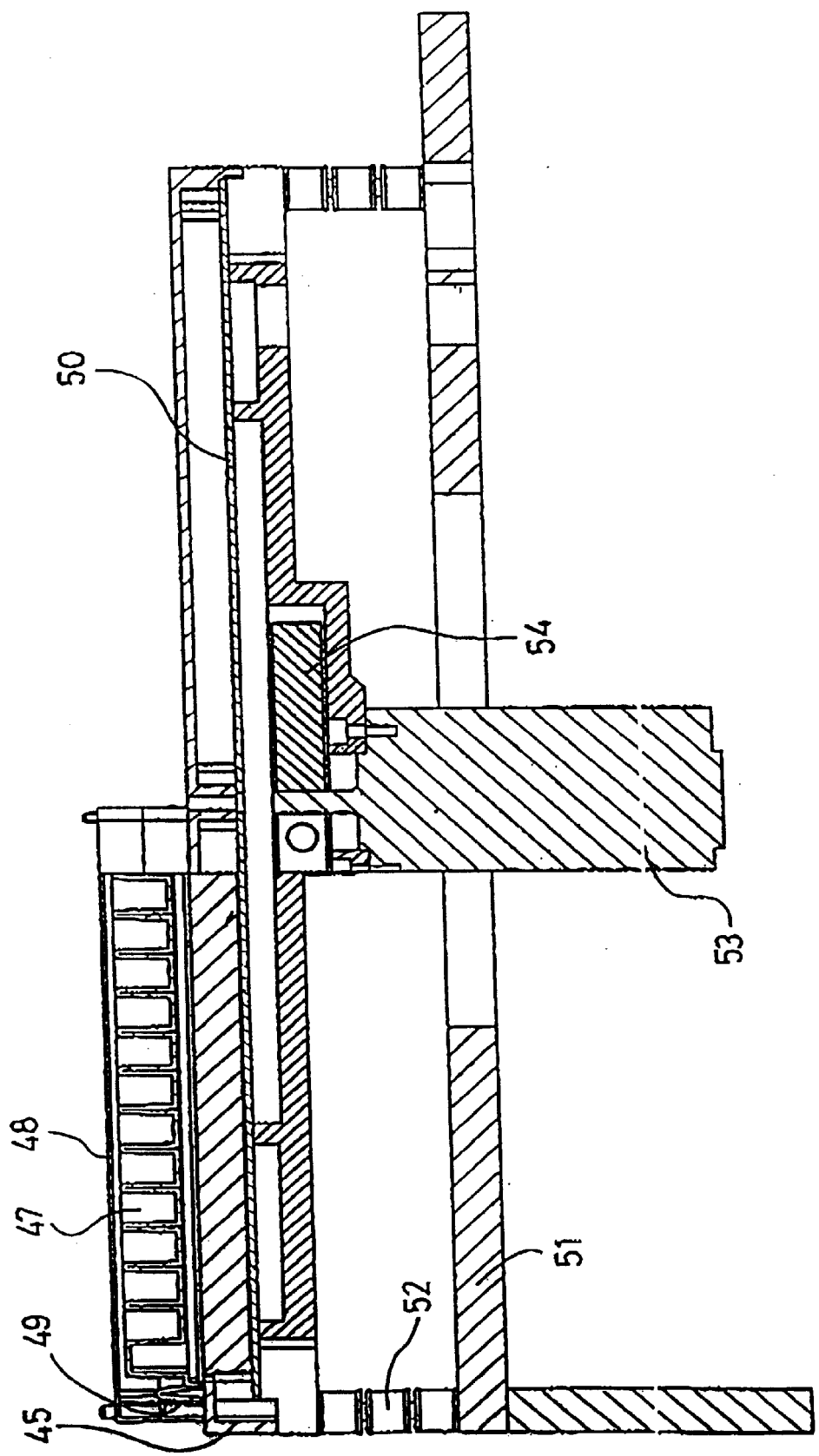
FIG. 11 is an explanatory section showing the arrangement of the support plate and the micro-titer plate.

Beneath the plate 45 there is a single printed circuit 50, FIG. 11, which has a surface resistor and a temperature detector for each region. The surface resistor is formed by a copper track 46 of the printed circuit 10 so that the required electrical resistance is achieved by control of its total length and its cross-section. Alternatively discrete elements may be used.

An electronic control circuit measures the temperature by means of a probe and regulates the energy in the resistor so as to achieve the temperature required for each region.

The said FIG. 11 shows a portion of the aluminum plate 45, a frame 49 and a lid 48 which form a cavity in which a micro-titer plate 47 is disposed.

As indicated, the frames have the function of rendering the various size and shape details of the micro-titer plates uniform to facilitate automatic handling thereof. Their other function, in conjunction with the lids and the aluminum plate 45, is to create the temperature-controlled chamber in which to perform incubations.

The lids also prevent excessive evaporation of the liquids contained in the micro-plate, particularly at higher temperatures.

If necessary, the positions of the frame and the lid may be reversed so that the micro-plate is situated on top of the frame, which is a thermal insulator, so that the micro-titer plate remains at ambient temperature.

The unit is mounted on a frame 51 by means of four resilient supports 52 so that the unit permits slight horizontal movements in the directions of the X and Y axes.

The frame 51 contains, in its central portion, a motor 53 the shaft of which has an eccentric load 54 so that, when the motor is set in operation, the set of incubators vibrates with a circular horizontal motion the elongation of which depends on the speed of rotation of the motor and on the excentric load thereof. This agitation system enables all of the wells of the micro-plates to be agitated uniformly.

Figure 14:
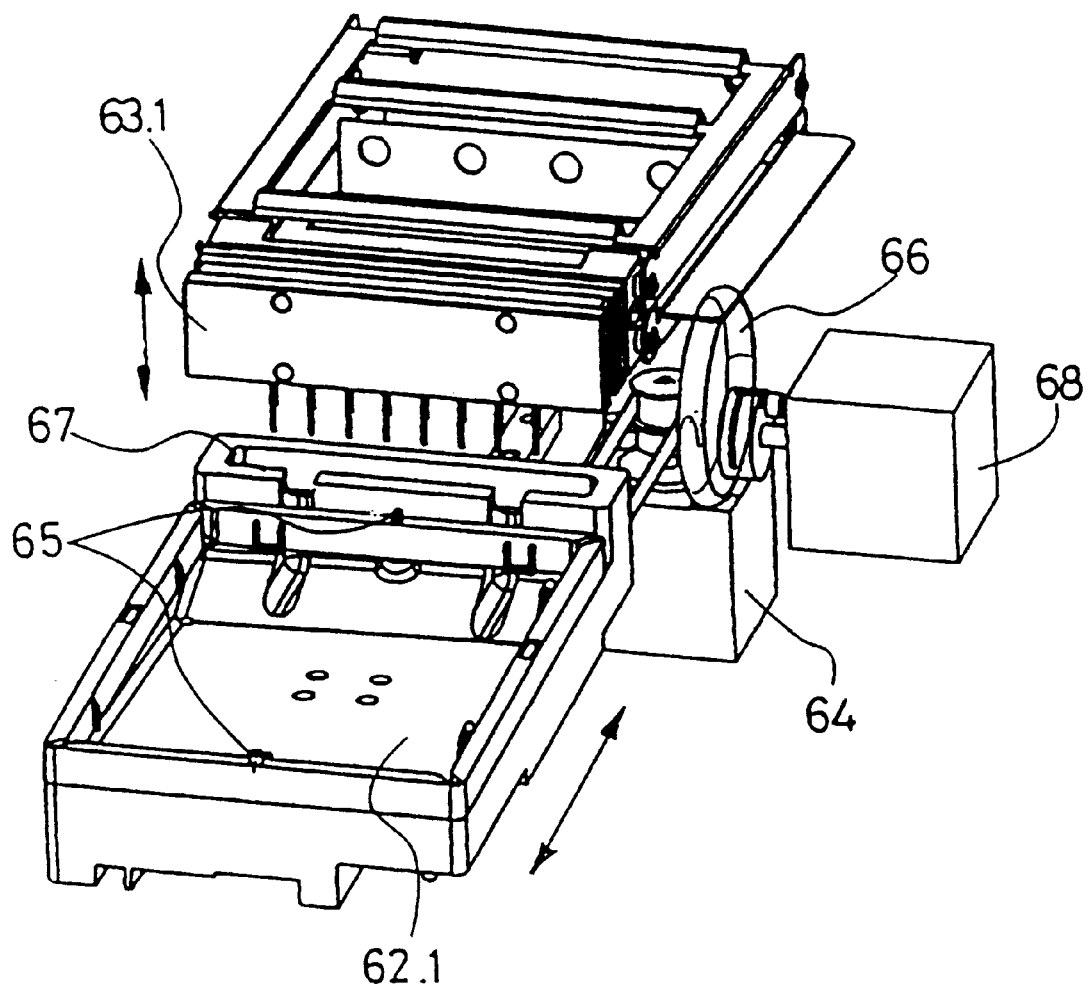
FIG. 14 is a simplified perspective view of the washing device of the apparatus.

The washing device shown in FIG. 14 is composed of a platform 62.1, which is movable in the Y direction by means of a motor 64 and a system of belts and which can house a frame with its micro-titer plate, for which the platform has locating elements 65, and a washing head 63.1 which is movable vertically by means of a pantograph system and a motor 68 with cams 66.

The movement along the Y axis enables the platform to be placed in different positions, the first of which enables the plate to be loaded with the use of a transportation system and the gripper or claw whilst the head 63.1 is situated above a container 67 for priming the system. The subsequent positionings of the platform enable the head 63.1 to be placed above each of the rows of wells of the micro-titer plate.

The head 63.1 can be seen in greater detail in FIG. 15 which shows a fixed portion 69 which has centering holes 74 and two holes coupled with respective tubes 75, one for the supply of the washing solution and the other for taking in the waste. A removable portion 70 has centering and fixing elements 76 and two tubes 77 for connection to the tubes 75.

The unit 70 is formed by three plates, the central plate 72 acting as a double cavity and the sides 71 and 73 as lids.

FIG. 16 shows the central plate 72 showing the specially shaped cavity 78 on one of the sides. There are eight separate capillary tubes 9 mm apart which project downwardly and are almost in contact with the elevations 80 of the cavity. A hole 81 communicates with one of the tubes 77. A toroidal seal 82 ensures the leaktightness of the lid 73. The unit is kept coupled by screws or by another method, not shown for greater clarity.

The cavity shown is used for aspiration and emptying of the wells of the micro-titer plate, this configuration enabling volumes to be minimized, permitting uniform aspiration in all of the wells, and preventing dripping of the head.

On the opposite face, not shown, there is a similar cavity with identical capillary tubes connected to the other tube 77 for the dosing of the washing solution. This second cavity as a whole is higher so that the lower capillaries are more elevated. The specific configuration of the cavity also avoids drips, equalizes volumes for all of the capillaries and enables the cavity as a whole to be primed by expulsion of the air remaining in the elevations 80 through the capillary tube with which they are almost in contact.

The reactions which take place by the combination of the samples with the reagents are measured by means of a photometer with a vertical beam which passes vertically through the wells of the micro-titer plate. In the apparatus of the invention, a single-channel reader is provided so that the reading of the plate is completed by ninety-six successive readings of different wells. A time study of each process of the apparatus shows that a single-channel reader, which may be mono-, bi-, or tri-chromatic, suffices to maintain the working rhythm, reducing the cost of the system.

The reader has a plate-loading position 83, FIG. 17 and, by means of two combined perpendicular movements, each of the wells of the plate can be positioned on the vertical axis, indicated 84, corresponding to the light beam of the photometer. A yoke 85 supports the light inlet 90 and the light-detector 89 which are aligned on a vertical axis 84. Two extreme positions 86 and 87 of the plate within the reader are shown. The plate moves beneath the washer and the incubator.

The configuration described optimizes the utilization of space since, according to a plan view, both the reader and the washer occupy the space of a single micro-plate in the loading position although after their movements they overlap at different levels, FIGS. 17 and 4.

The light source and the system of filters are located in another part of the apparatus, the monochrome light reaching the yoke 85 via a bundle of optical fibres so that better use can be made of the space and the heat of the lamp can be dissipated where it does not interfere with the devices of the apparatus.

The regions 33 and 34 indicated in FIG. 4 act as stores for lids and stores for finished plates. The user can normally gain access solely to a region 34 in order to withdraw the used frames and plates and to recover the frames for subsequent use. The lids, on the other hand, normally remain in the store 33 and the apparatus itself uses them and stores them as required.

Given that both the lids and the frames are stackable in these positions, an indefinite number of plates and lids can be kept.

Figure 18:
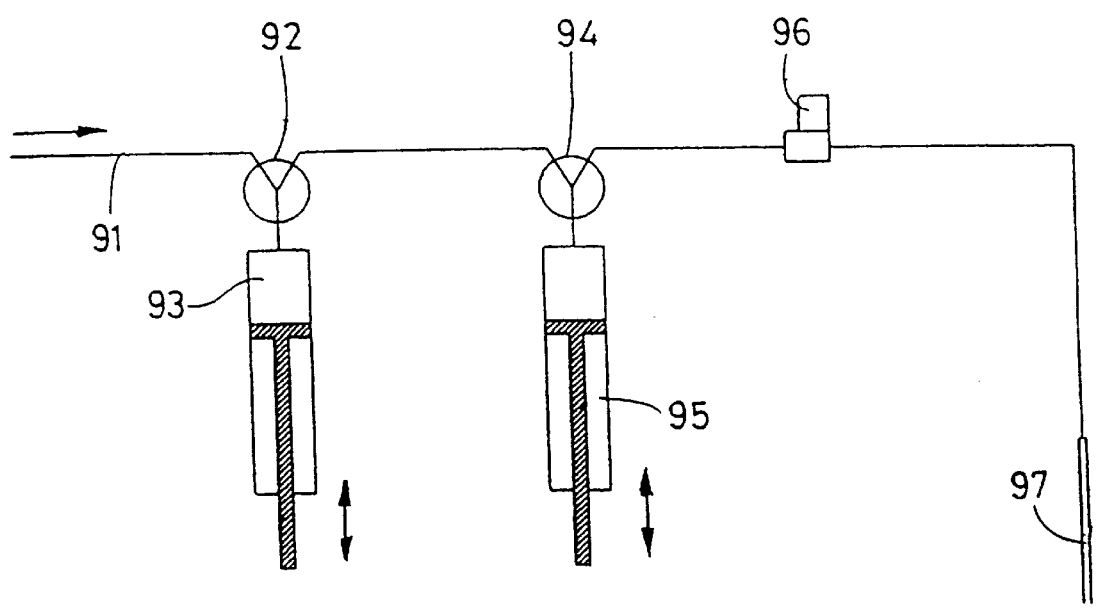
FIG. 18 shows schematically a sampling system.
Figure 19:
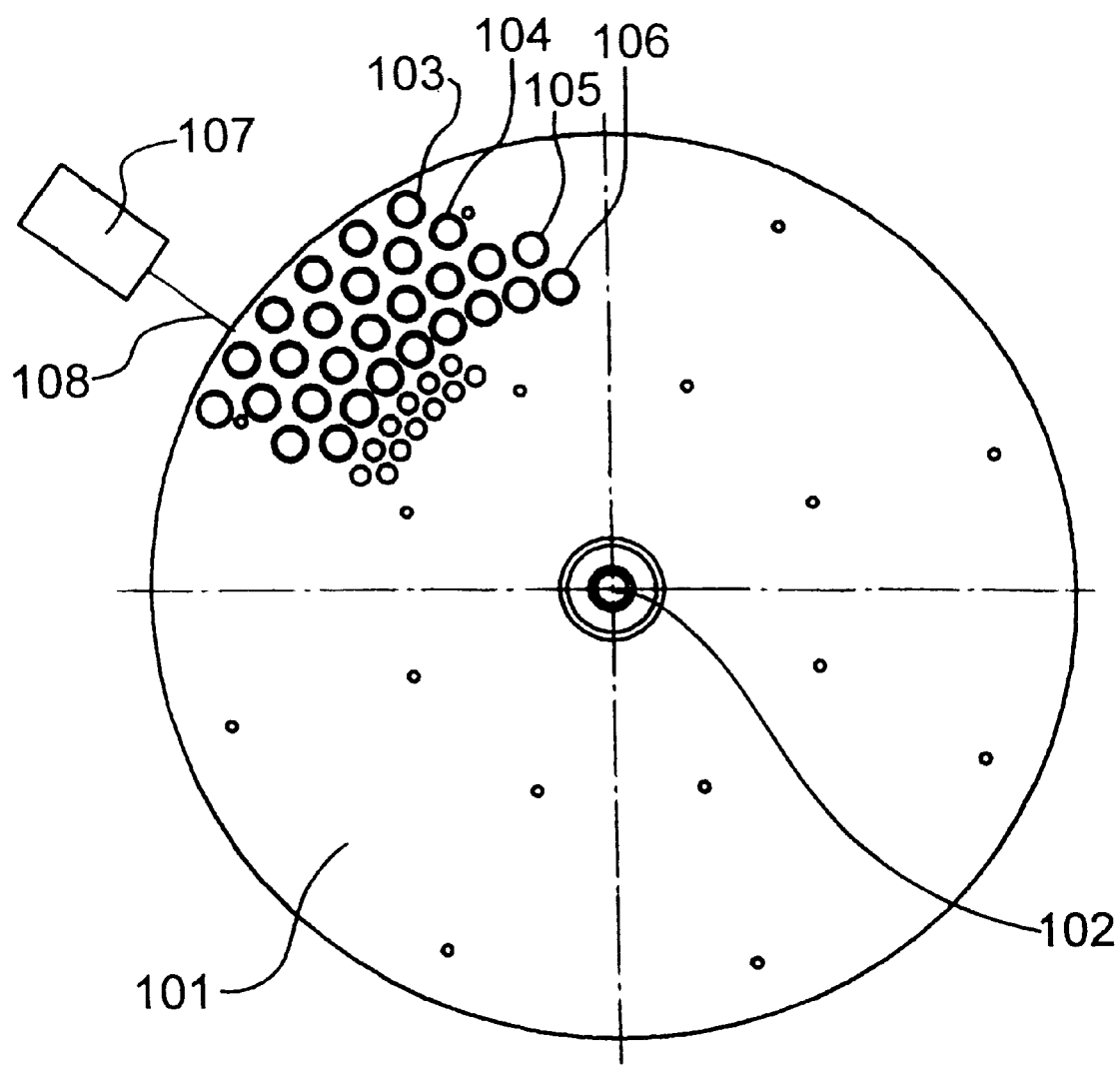
FIG. 19 is a plan view of a rotatable plate provided with a plurality of concentric rings holding the test tubes.
Figure 20:
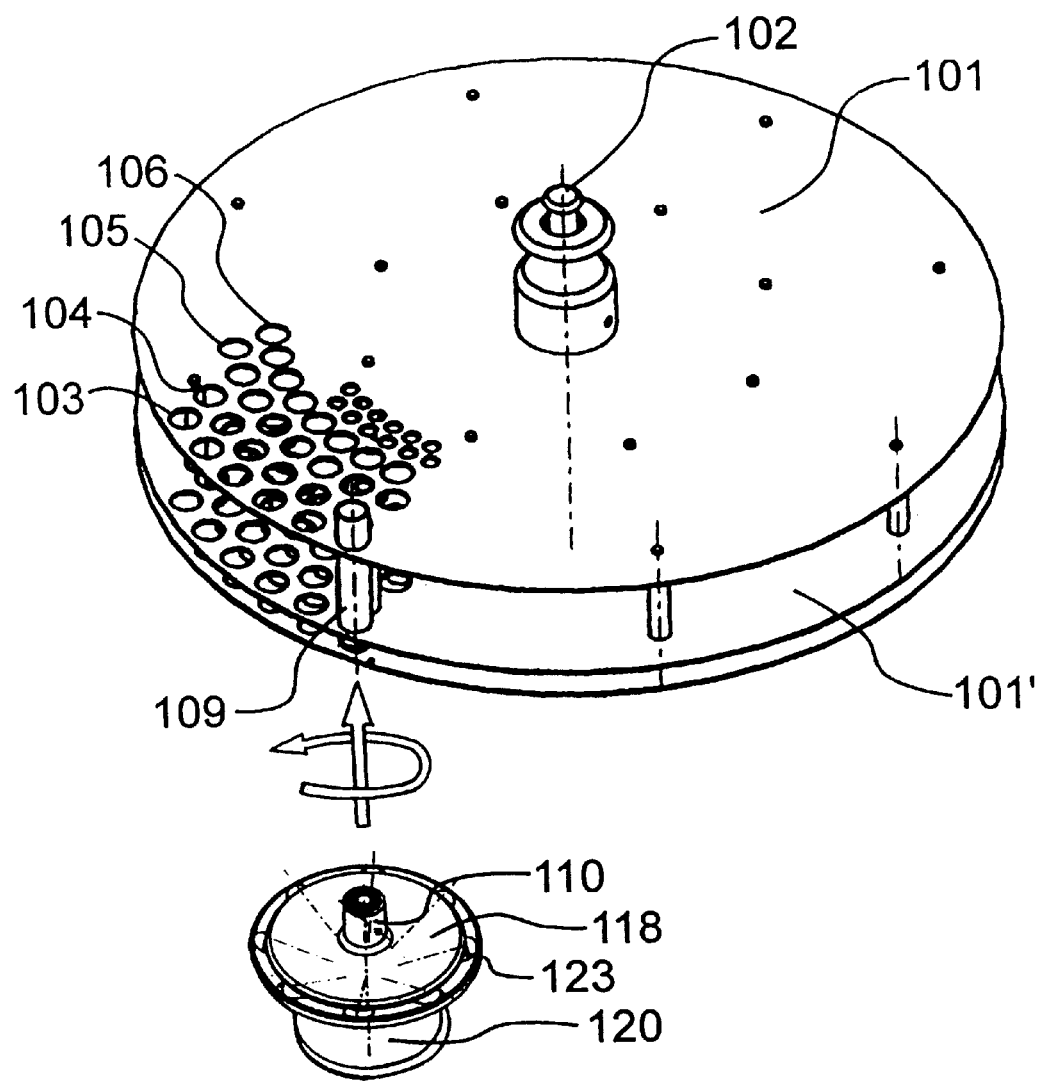
FIG. 20 is a perspective view of the rotatable plate of FIG. 19 and of a device which can rotate each individual tube.
Figure 21:
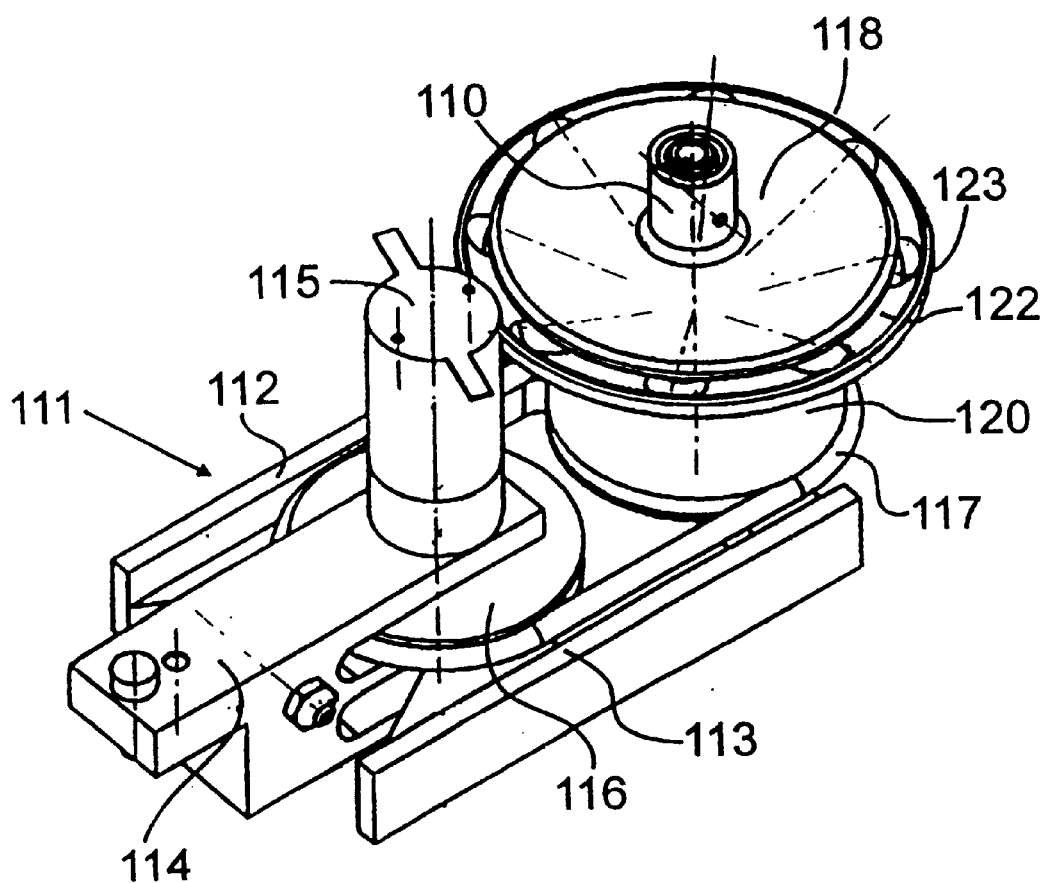
FIG. 21 is a perspective view of the device for rotating the tubes.
Figure 22:
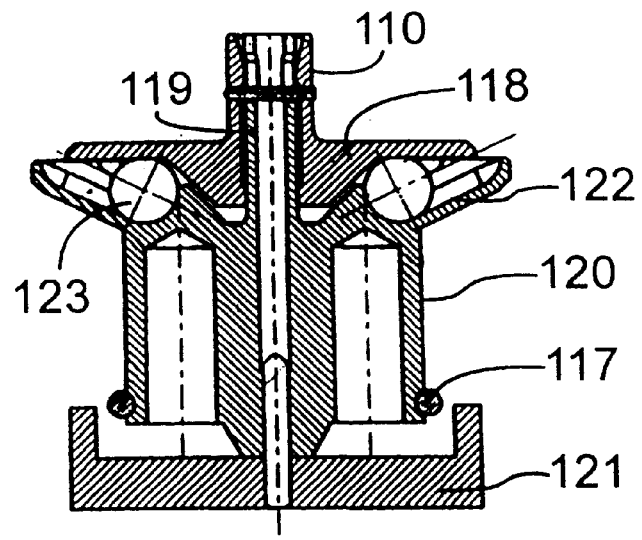
FIGS. 22 and 23 are respective schematic sections of the device for rotating the sample tubes.
Figure 23:
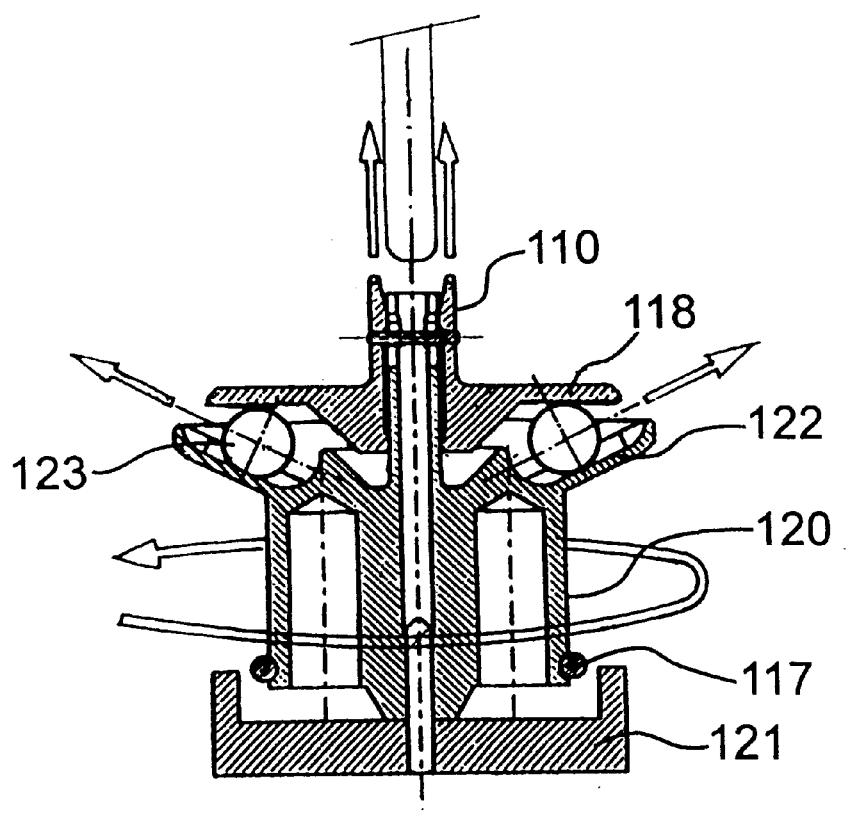

The fluid system of the apparatus is constituted by various relatively independent subsystems. In the first place, there are two sampling systems, FIG. 18, each constituted by a supply of a solution 91 coming from any one of the reservoirs of washing solutions of the system, connected to two numerically-controlled probes, one large-volume syringe 93 and another small-volume syringe 95, through two zero dead-volume, three-way valves 92 and 94 which are also numerically controlled. A pressure transducer 96 enables the moment at which the clogging of the probe 97 takes place to be measured. The washing solution which fills the circuit is selected by a set of valves which interconnect the inlet 91 with each of the supply reservoirs. According to the positions of the valves 92 and 94 and by means of the movements of the probes 93 and 95, the circuit is primed, and small quantities of liquid are aspirated and dosed precisely by means of the probe 97 with the syringe 95, or larger quantities with less precision by means of the syringe 93.

There is a tip-washing station in the form of a container with a liquid inlet and outlet (see FIG. 4, reference numeral 36). The inlet is connected to one of the washing solutions by means of various valves and the outlet is connected to the waste tank. The probes can be immersed in this container and washed externally as well as internally by causing washing solution to flow from their interior.

In the washer, which is also connected to the waste tank, there is a drain for primings and possibly overflows.

The washer has a series of valves for selecting the appropriate washing solution which is supplied to the washing head. The capillary tubes of the head take in the waste from inside the wells and direct it to the waste tank.

The reservoirs of washing solutions are subject to a constant air pressure so that the liquid contained is circulated when the valves of their output circuit are opened. There is therefore an air compressor and a pressure regulator.

The waste tank is subject to vacuum so that the waste can be taken into it by suitable valves. A vacuum pump with its regulation system is therefore connected to this tank.

FIGS. 19 to 30 show details of the rotatable plate or carousel of the apparatus of the level detector device, and of the containers, appropriate reference numerals being used for elements corresponding to those of in FIGS. 1 to 18. The plate or carousel 101 of the present invention is rotatable about its central axis 102 and has a plurality of rings of circular holes such as 103, 104, 105, 106, . . . in which tubes carrying samples can be disposed. A head 107 for reading identification marks of the tubes faces the sample tubes of the plate or carousel 101 along a detection axis 108 which is preferably but not exclusively radial relative to the plate 101.

The present invention provides for each of the sample tubes 109 to be rotated when it passes in front of the reading head 107 so that as it rotates about its own axis at least once whilst it is in the field of view of the head 107, thus ensuring that the inscriptions produced on the sample tube 109 pass at least once in front of the reading head in a manner effective for the reading to take place, avoiding the errors which are possible at the moment with known methods and apparatus.

Given that the carousels carrying the tubes are generally composed of several plates such as the plate 101 indicated above and a second parallel plate 101' of similar characteristics for adequate support and guiding of the tubes 109, the method of the present invention provides for the tube 109 to be raised along its axis so that it can be rotated more easily and for the rotation of the tube about its axis then to be brought about in the manner explained, the tube subsequently being replaced on the lower plate 101'.

The present invention preferably provides for the arrangement of a rotatable element or rod 110 movable vertically upwards and downwards on an axis which coincides with that of the tube 109, bringing about the rotation of the tube at the desired moment.

In a preferred embodiment, the rotatable rod 110 is incorporated in a framework 111 which can bring about a movement in order to cause the rod 110 to establish contact with the tube 109 and to withdraw it from this contact, the framework having a construction based on two arms 112 and 113 and on an inner pivoting assembly 114 on which an electric motor 115 brings about rotation of a pulley 116 which, by means of a belt 117, in turn brings about rotation of the rod 110 which causes rotation of the tube 109. The rod 110, for its part, forms part of a plate 118 which is rotated by a drive pin 119 of a lower rotatable body 120 the lower portion 121 of which is driven by the belt 117 from the pulley 116 of the motor.

In order to bring about the upward and downward movement of the rod 110, the body 120 has a frustoconical upper region 122 housing a series of balls 123 which act on the lower surface of the plate 118. When the body 120 rotates, the centrifugal force thus brings about a radial movement of the balls 123 which, as the balls are moved on the frustoconical region 122, is translated into a lifting of the plate 118 and of the rod 110 which establishes contact with the lower end of the sample tube 109.

So that the unit 111 can act on sample tubes of different rings of holes of the carousel 101, the unit 111 has to be moved in order to gain access to one or other ring of holes. In a simplified embodiment, this can be achieved by the rotation of the device 111 about a vertical axis so that the rod 110 which brings about the rotation of the tubes can coincide with the appropriate point which corresponds to different rings of holes, thus being able to work on one or other of the rings whenever the tubes of the said rings of holes are visible by the reader head 107.

Figure 24:
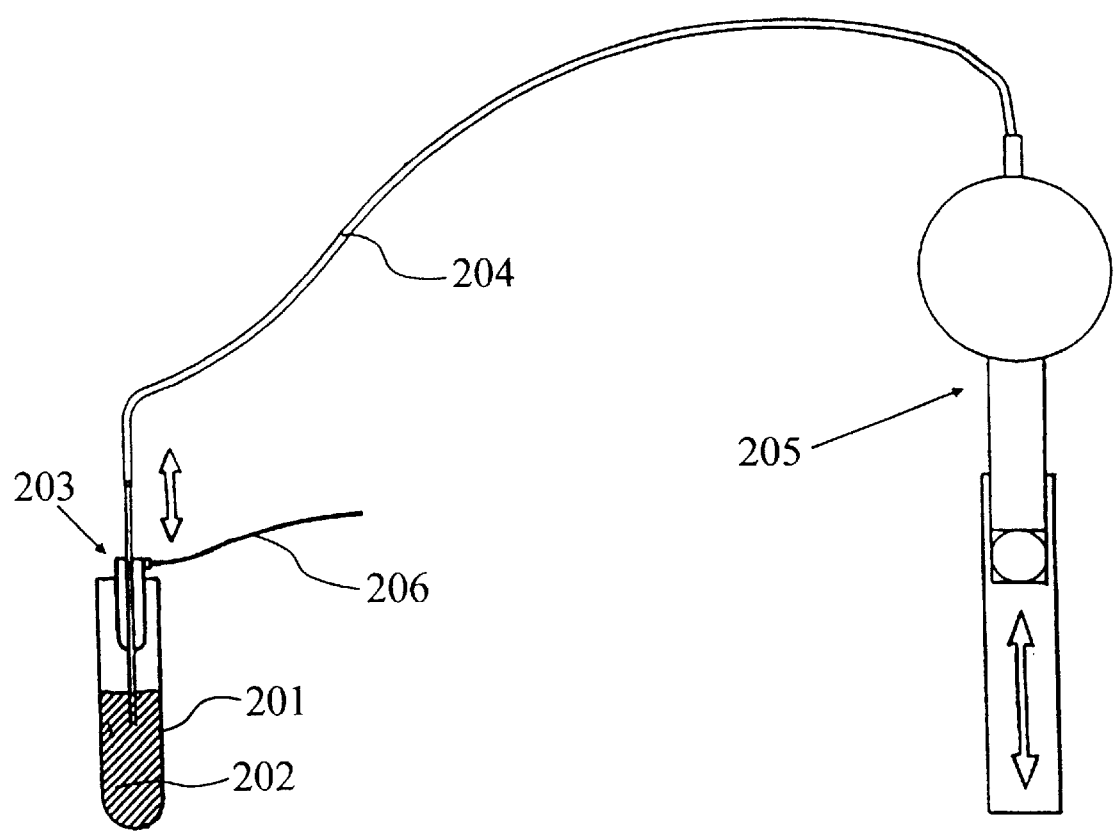
FIG. 24 shows schematically an arrangement of means which connect a pump to a syringe disposed in a sample tube.
Figure 25:
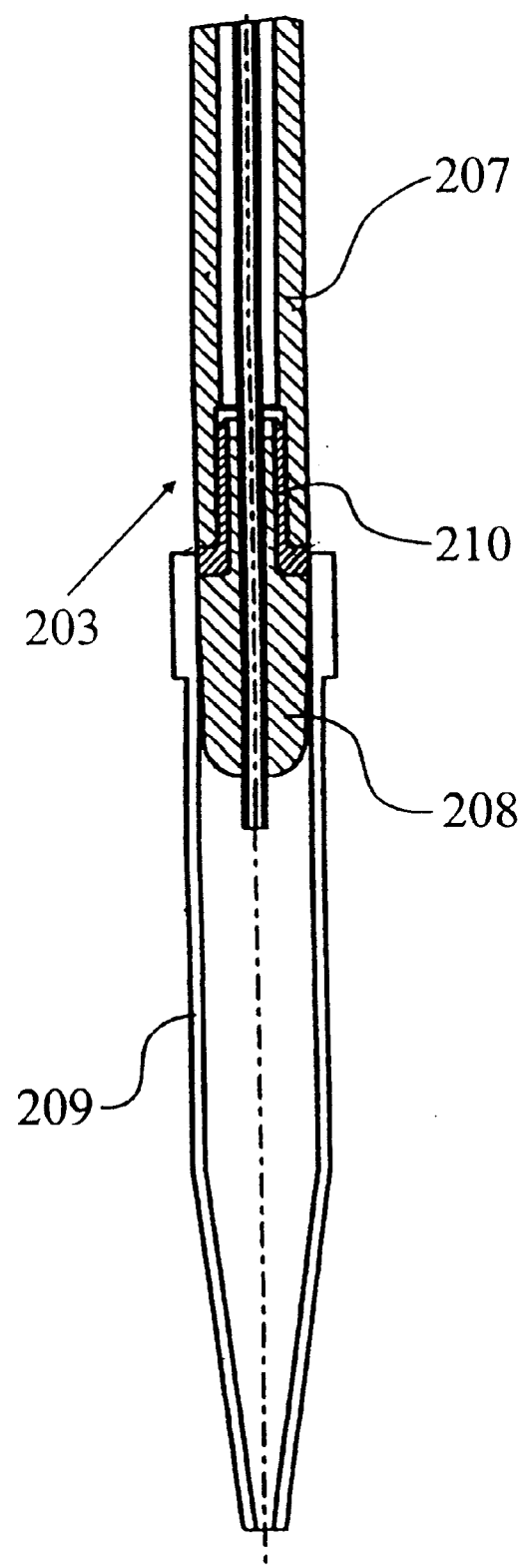
FIG. 25 is a section through the syringe of the present invention.
Figure 26:
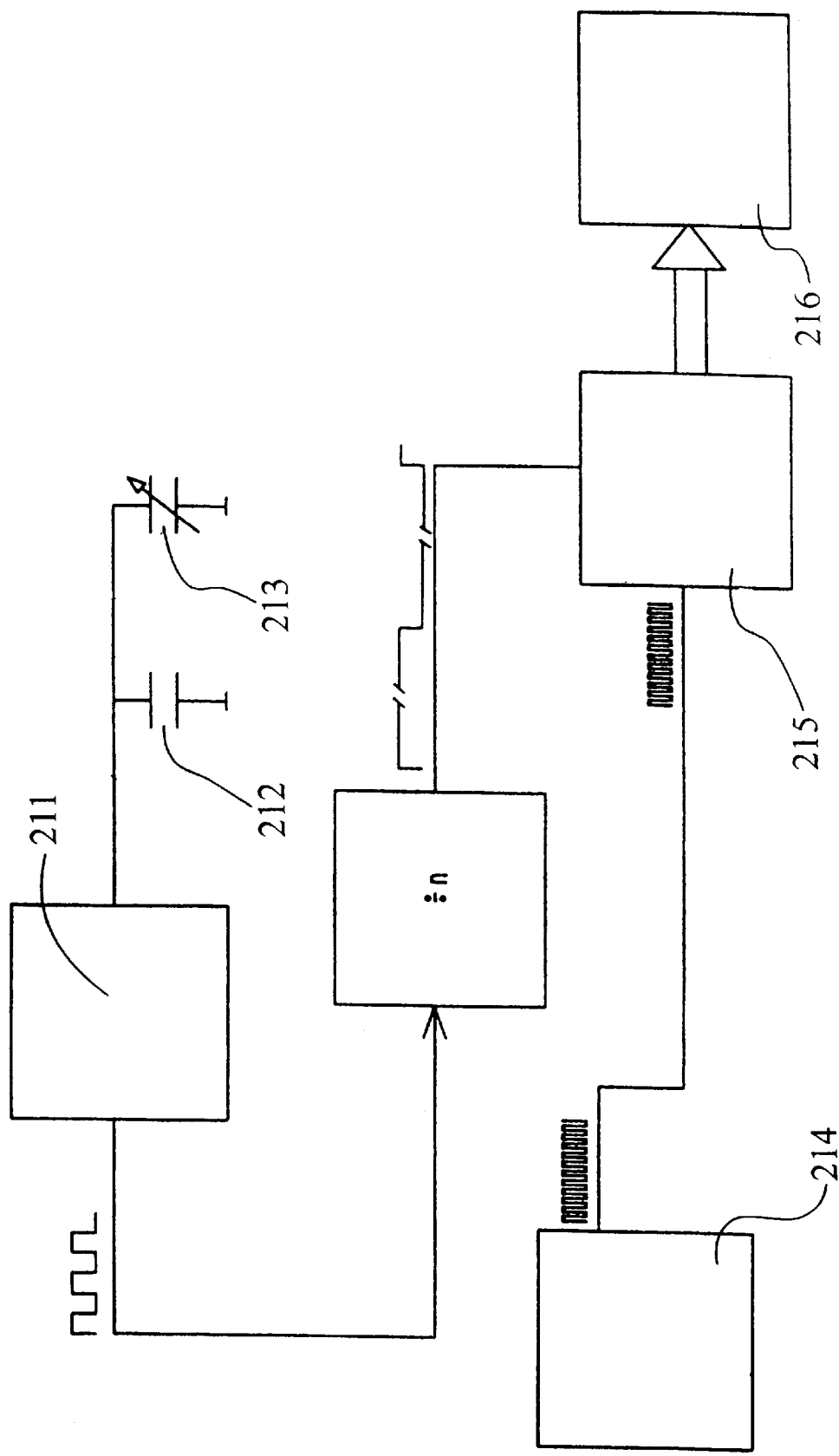
FIG. 26 is a diagram of the electronic portion of the level detecting device of the invention.
Figure 27:
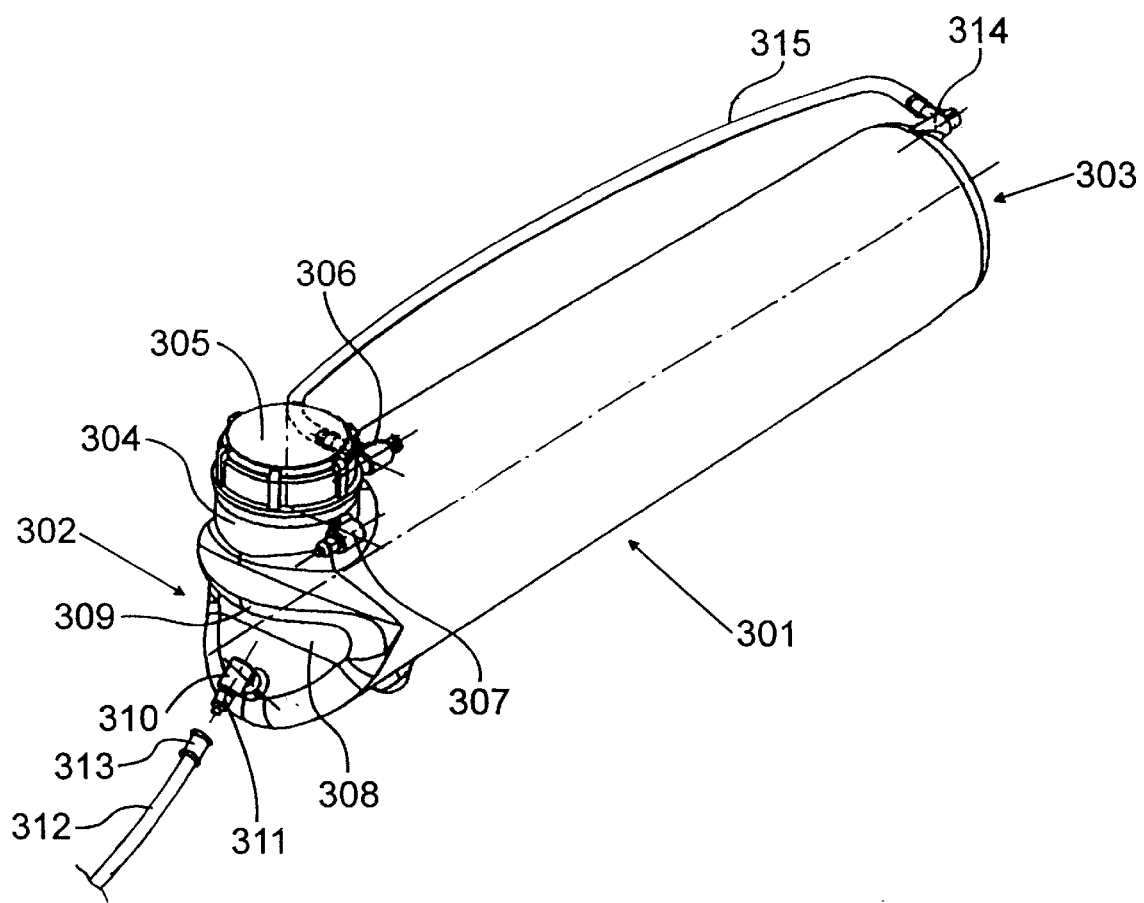
FIG. 27 is a perspective view of a container for liquids according to the present invention.
Figure 28:
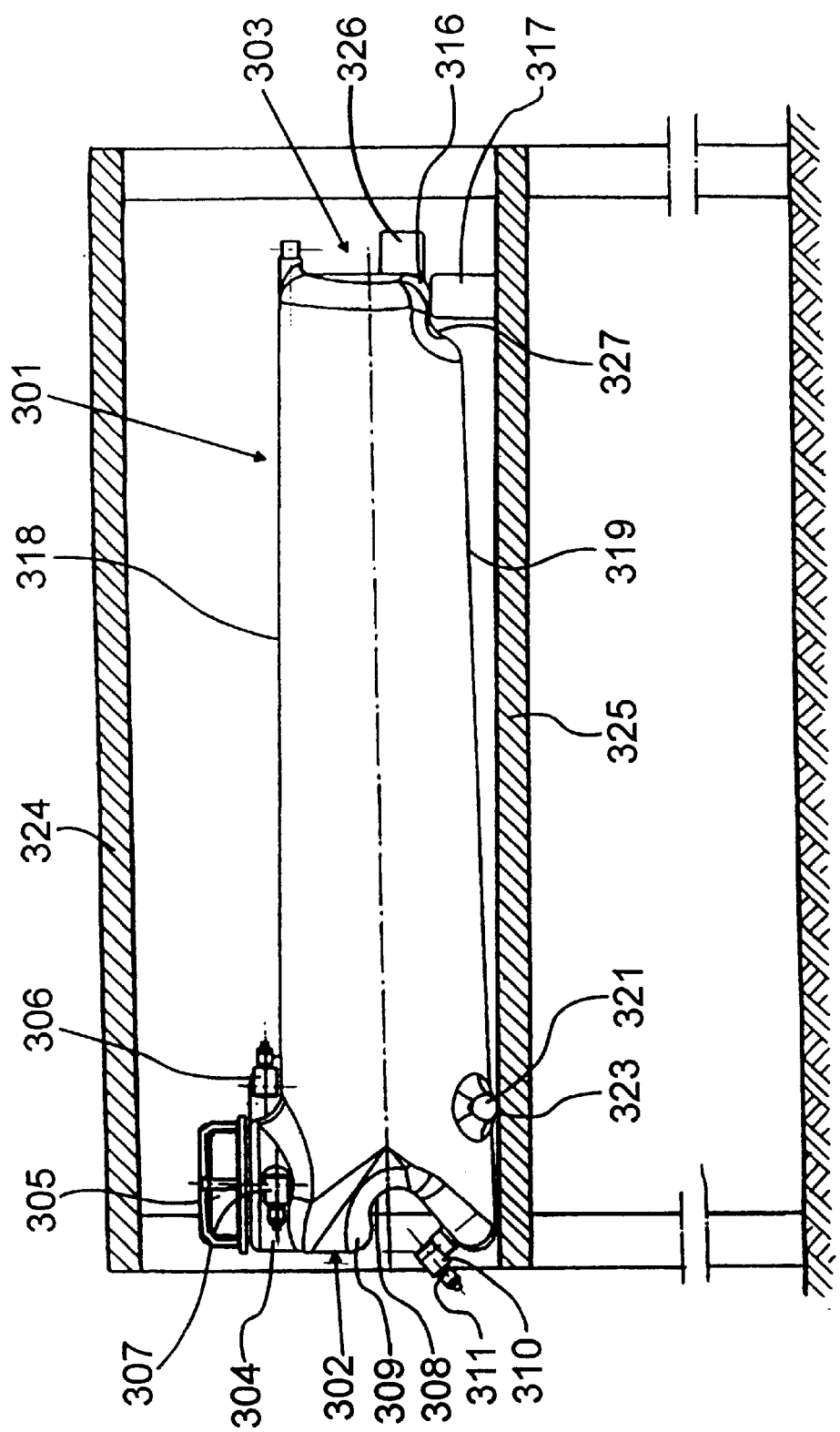
FIG. 28 is a longitudinal section through the container in the position of use.
Figures 29, 30:
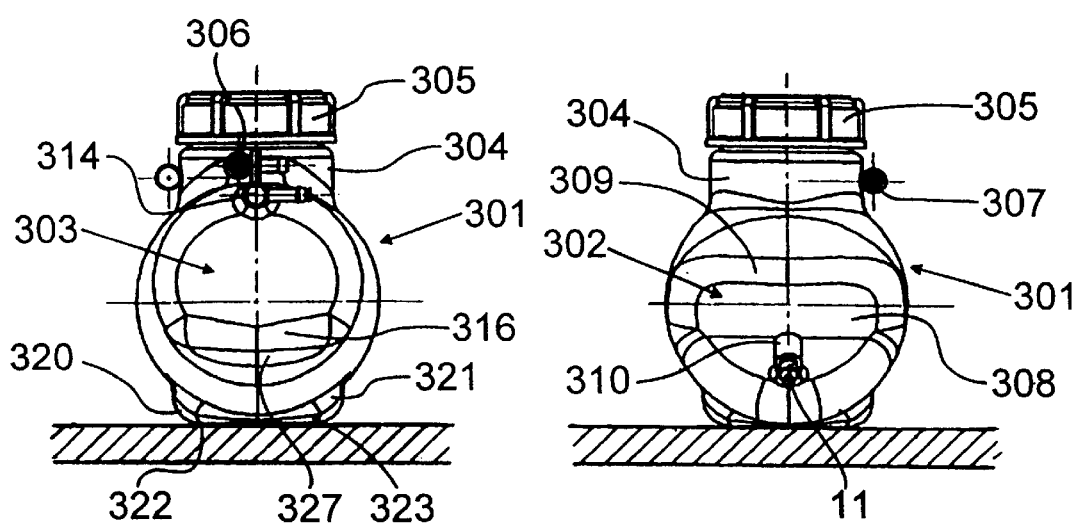
FIGS. 29 and 30 are elevational views of the container of the invention from the rear and from the front, respectively.

As can be appreciated from FIGS. 24 to 26, the manipulation and level-detection device is fitted on tubes 201 carrying sample liquids 202 with the use of a syringe 203 which is connected to a tube 204 for drawing in liquids, which preferably operates by means of a pump, generally indicated 205. The syringe is also connected to the electronic control unit by means of a wire 206.

As can be seen in FIG. 25, the syringe unit 203 has the structure of a wholly or partially metallic, tubular element 207 which is coupled to a cone 208, possibly for receiving disposable tips 209 which can be fitted and removed mechanically, the tubular element 207 being coupled to the cone 208 with the interposition of an insulating cap 210 for reducing the capacitance of the syringe as much as possible to achieve greater accuracy.

The electronic control unit of the device comprises a first oscillator 211 connected to a fixed capacitor 212 and to a variable capacitor 213 represented by the syringe, so that the oscillator oscillates at a frequency which depends upon the capacitance and which, by way of example, may be between 100 and 500 KHz. As indicated above, when the syringe is placed in contact with or approaches other conductor bodies, such as the liquid in the container or a disposable tip, its capacitance increases so that the oscillation frequency decreases. Monitoring of the variation of this frequency can indicate contact or proximity with other bodies, which is utilized in this device to detect the liquid disposed in a container or to detect the conductive disposable tip. Since this is a cumulative process, the system detects the contact with the disposable tip if it is used and, subsequently, contact with the liquid. In order for the device to have high sensitivity, the electrical capacitance of the syringe is made as low as possible so that the subsequent variations in frequency are higher as percentages, this being achieved partially by the insulation of the end of the conductive syringe 208 from its remaining portion by means of the above-mentioned cap 210. The device comprises a second, fixed oscillator 214, the activation frequency of which is much higher, for example, 10 MHz, and in which the counting of the frequency is performed during a window period corresponding to a predetermined number of cycles of the syringe oscillation frequency, for example, 100 cycles. This count corresponds inversely to the syringe frequency so that the syringe oscillation frequency can be determined precisely during each counting period. The signals of the counting device 215 are passed to the microprocessor 216 which applies various algorithms in order to decide when a level is detected, when a tip is present, or other characteristics according to the requirements of the process. Noise-reduction systems are also used if necessary.

The device is self-adaptive in the actual conditions of the system, the microprocessor being able to adapt the absolute and relative decision thresholds automatically according to the instantaneous conditions of the system, eliminating adverse effects which arise, for example, owing to ambient humidity.

The device uses basically two algorithms, the first of which detects when, during the lowering of the syringe, it comes into contact with the liquid or another element such as a disposable tip, etc. In this case, the syringe starts to descend and, at a predetermined moment, a mean frequency is obtained for use as a reference. The syringe continues to descend, the frequency being monitored by the method mentioned until a variation is observed which is greater than a certain threshold at which the position of the syringe is determined.

The second algorithm is used to check that the disposable tip has not been removed during use, taking as a reference the oscillation frequencies when the syringe has picked up the disposable tip. Verification that the frequency is maintained within predetermined limits can subsequently be performed, confirming the presence of the disposable tip.

According to FIGS. 27 to 30, the present invention includes the construction of a special container 301 for holding liquids used in the apparatus, the container being of elongate structure and variable material, although it is preferably made of a suitable plastics material, its front end or head 302 and its rear end or base 303 being moulded and having characteristics specific to their function. According to the present invention, the front portion or head 302 of the container has an upper opening 304 with a lid 305, affording access to the interior of the container, having fixed couplings with valves 306 and 307 for the incorporation of respective connectors for various uses such as for the inlet of liquid or connection to a pressurized fluid supply, or to a vacuum source. The front head 302 of the container has a large moulded recess 308 forming an upper region 309 with handle-like characteristics for enabling the container to be lifted and handled easily. The head 302 has, in its lower front portion, a coupling 310 for a liquid-outlet connector 311 to which an outlet pipe 312 having a quick coupling 313 can be coupled. All of the outlet or inlet connectors of the container have valves which close automatically when the pipe is disconnected thus allowing the container easily to be connected to and disconnected from the corresponding pipes, the container remaining closed without the need for awkward manipulation operations as are currently required with known containers.

The rear end 303 also has a fixed outlet 314 for a connector of a similar nature to those mentioned above, possibly connectible by means of a pipe 315 to one of the front connectors 306 to facilitate the handling from the front end. The rear head itself has a lower step 327 having a bevelled and/or rounded rear region 316 for facilitating rearward insertion of the container from the front.

The rear step 327 fits in a support or mounting 317 of a loading cell, enabling the degree of filling of the container to be monitored.

The moulded structure of the container provides for the container to have, in its working position, its upper surface 318 substantially horizontal and its lower surface 319 inclined forwardly from the rear to permit more complete emptying of the container through the front connector 311.

On the front portion or head 302 of the container, there are lower projections 320 and 321 preferably forming a single body but defining two separate bearing points such as 322 and 323 for the container.

The container of the present invention is intended to be located beneath the table 324 of automatic apparatus for testing samples or other similar apparatus, being supported on a lower partition wall 325 and extending practically for the entire width of the table which in practice determines the length of the container 301. For improved positioning of the container, the cell in which it is disposed has a rear abutment 326 which establishes the axial position of the container which is easily introduced from the front portion of the cell.

What is claimed is:

1. Apparatus for performing laboratory tests automatically comprising:

a first main region of equipment and a second main region of equipment, operation of the equipment in each region being controlled separately, the first region, to which the user has interactive access, permitting loading of a plurality of samples, controls, calibrators and diluents for performing the sampling and the dilutions, and receiving a plurality of plates on which a plurality of tests are performed, and the second region, to which the user has selective access, comprising a plurality of stations permitting stages of the tests including at least incubation, washing and, reading, the second region being able to hold at least two plates at different stages of the testing, the apparatus having means for automatically moving the plates along three coordinate axes X, Y, Z in order to transport the plates to complete the testing, for enabling several tests to be performed at the same time on a set of samples on one or several plates, and for enabling a new series of tasks with the same or different sets of tests and the same or different sets of samples to be started even when the previous ones have not been completed, the apparatus comprising, beneath the first and second main regions, a series of containers for storing a plurality of auxiliary liquids;

wherein the automatically moving means includes a carriage movable on two horizontal guides along the X and Y axes, the carriage being movable on a vertical Z-axis guide and carrying a plurality of probes for the manipulation of liquids, the probes incorporating individual level detectors, the carriage also having an independently vertically movable gripper for picking up the plates, enabling the plates to be moved to a new position, and for depositing the plates in a predetermined location.

2. Apparatus for performing laboratory tests automatically according to claim 1, wherein the vertically-movable carriage includes a system for the ejection and recovery of disposable tips that is incorporable in the probes.

3. Apparatus for performing laboratory tests automatically according to claim 2, wherein the probes extend through the body of the carriage movable on the Z axis, through holes for the sliding of the probes, the diameter of the holes being smaller than that of the disposable tips which are ejected automatically by the body of the carriage during the upward movement of the probes.

4. Apparatus for performing laboratory tests automatically according to claim 1, wherein each probe includes a syringe composed of an enveloping body carrying internally a capillary tube for collecting samples as well as a cone for receiving disposable tips which is mechanically connectable and disconnectable, the syringe, which acts as a variable capacitor, being connected to a low-frequency oscillator connected to a second oscillator of much higher frequency by means of a counting device which performs a frequency count during a window period corresponding to a predetermined number of cycles of the oscillation frequency of the first oscillator in order to measure precisely the variable frequency of the first oscillator, the count signal being passed to a microprocessor for determining the level-detection, the presence of a disposable tip.

5. Apparatus for performing laboratory tests automatically according to claim 4, characterized in that the syringe has an insulator between the carrying body and the cone for the coupling of the disposable tips, in order to reduce the capacitance of the syringe and to increase the accuracy of measurement.

6. Apparatus for performing laboratory tests automatically according to claim 4, wherein the capillary tube inside the syringe extends through the cone for the coupling of the disposable tips and extends beyond the cone to permit direct taking of samples.

7. Apparatus for performing laboratory tests automatically according to claim 1, further comprising a plurality of frames for receiving the plates, the frames having coupling elements for coupling with the carriage movable along the Z axis, and enabling receipt of suitable closure lids for protecting the plates and for preventing evaporation, the lids also having couplings and locating elements for enabling the lids to be picked up automatically by the carriage movable along the Z axis.

8. Apparatus for performing laboratory tests automatically according to claim 1, characterized in that the carriage movable along the Z axis has an assembly with two hooks which is pivotable on a horizontal axis, the hooks being insertable in corresponding slots of the frames carrying the plates and the lids, for the grasping and manipulation thereof.

9. Apparatus for performing laboratory tests automatically according to claim 1, wherein the first region being provided with separate functional control has a carousel which carries sample tubes and reagent containers and to which a device is coupled for rotating the sample tubes on their own axes for the reading of the bar-codes of the tubes, a plate being lowerable and being enabled to receive a plate-holder frame associated with the first region.

10. Apparatus for performing laboratory tests automatically according to claim 9, characterized in that the carousel of the first region has in succession from the outside towards the interior, alignments of holes for sample tubes and for tubes for forming pre-dilutions, housings for the disposable tips for the sampling and dilution operations, and housings for calibrators, controls and diluent.

11. Apparatus for performing laboratory tests automatically according to claim 10, wherein the carousel is removable, enabling a first carousel to be prepared independently of a second carousel that is being processed in the apparatus.

12. Apparatus for performing laboratory tests automatically according to claim 1, further comprising a system of optical sensors having means for checking for the presence on a carousel of sample tubes of dilutions, of disposable tips and of controls, calibrators, and diluents with a plurality of optical reflection detectors that emit light beams which are slightly offset relative to the central axis of an element supported in order for the light beam to be deflected sideways, preventing the light beam from passing through the tube or disposable tip.

13. Apparatus for performing laboratory tests automatically according to claim 11, characterized in that the containers for diluents have a transversely oval structure to allow two probes to enter at the same time.

14. Apparatus for performing laboratory tests automatically according to claim 1, characterized in that the second region of the apparatus comprises, accessible directly by the carriage, a set of several incubation/agitation stations, a plate-washing station, a reading station, a lid-storage station, a station for the storage and output of processed plates, a tray carrying reagents and disposable tips for probes, a container for collecting ejected disposable tips and a station for washing disposable syringe tips.

15. Apparatus for performing laboratory tests automatically according to claim 14, characterized in that the reagent-carrying tray of the second region of the apparatus is situated adjacent the first region and has a region for holding a plurality of reagent containers as well as a region for holding the disposable tips for the probes and the container for the ejection of disposable tips as well as the station for the washing thereof.

16. Apparatus for performing laboratory tests automatically according to claim 14, characterized in that the incubation and agitation stations have respective heating regions insulated from one another and controlled separately to permit operation with different temperatures therein.

17. Apparatus for performing laboratory tests automatically according to claim 16, characterized in that each of the incubation/agitation stations has independent locating elements for permitting the insertion of frames carrying plates or lids for the closure thereof.

18. Apparatus for performing laboratory tests automatically according to claim 16, characterized in that, beneath the plate supporting the incubation/agitation stations, there is a single printed circuit with a surface resistor and separate temperature sensor for each region, enabling the temperature of the region to be controlled.

19. Apparatus for performing laboratory tests automatically according to claim 18, characterized in that the surface resistor is formed by a track of conductive material of the printed circuit, enabling the electrical resistance to be varied by control of the total length and cross-section thereof.

20. Apparatus for performing laboratory tests automatically according to claim 19, characterized in that the surface resistor is constituted by discrete elements.

21. Apparatus for performing laboratory tests automatically according to claim 14, characterized by a frame fixed to the frame of the apparatus by means of resilient supports, a motor incorporating an eccentric mass which enables the plates to be vibrated at the incubation stage.

22. Apparatus for performing laboratory tests automatically according to claim 14, characterized in that the plate-washing station comprises a platform which is movable in the Y direction by means of an independent motor and a system of belts, and housing a frame with its plate for which the platform has locating elements, the plate-washing station also comprising a washing head movable vertically by means of a pantograph system and an autonomous motor with an eccentric device.

23. Apparatus for performing laboratory tests automatically according to claim 22, characterized in that the head of the washing unit comprises a fixed portion with locating holes and two holes connected to respective tubes for the supply of the washing solution and for taking in the waste, respectively, and a releasable portion which has two locating and fixing elements and two tubes for connection to the aforementioned tubes.

24. Apparatus for performing laboratory tests automatically according to claim 23, wherein the releasable unit is formed by three plates of which the central one has a double cavity and the lateral ones act as lids, one of the sides having a series of raised portions, and having in its lower portion a hole which communicates with one of the tubes of the lateral lids of the unit formed by the three plates, the cavity being used for aspiration and emptying of a plurality of wells of the plate, and the opposite face of the unit having a similar cavity with similar capillary tubes connected to the tube for dosing the washing solution.

25. Apparatus for performing laboratory tests automatically according to claim 24, further comprising a photometer with a vertical beam which passes vertically through the wells of the micro-plate, constituting a single-channel reader for reading each of the wells of the micro-plate, with a plate-loading position, with the capability for all of the wells of the plate to be located, by combined perpendicular movements, on the vertical axis of the reading beam, on which a yoke keeps a light inlet and a light detector aligned vertically at the cell-reading point.

26. Apparatus for performing laboratory tests automatically according to claim 25, characterized in that a light source and a system of filters is located separately from the light-beam reading device, the light being conducted to the yoke carrying the beam and the light detector by means of a bundle of optical fibres, optimizing space and reducing the generation of heat in the device.

27. Apparatus for performing laboratory tests automatically according to claim 1, further comprising a fluid system which has two sampling systems each constituted by a supply of a solution coming from any of the reservoirs of washing solutions of the system, connected to two numerically-controlled probes, one of large volume and the other of small volume, by means of two zero dead-volume three-way valves which are numerically controlled, and having a pressure transducer for measuring any stopping-off of the probe.

28. Apparatus for performing laboratory tests automatically according to claim 27, further comprising a station for washing the tips for the probes, in the form of a container with a liquid inlet and outlet, the inlet being connected to one of the washing solutions by means of valves and the outlet being connected to the waste reservoir, the container being able to admit the probes for external and internal washing thereof.

29. Apparatus for performing laboratory tests automatically according to claim 28, characterized in that the reservoirs with washing solutions are subjected to a constant air pressure to enable the liquid to be circulated when their outlet valves are opened, and in that the waste reservoir is subjected to vacuum to cause waste liquids to be drawn into the waste reservoir, the apparatus comprising compression and air-pressure regulator, and a regulated vacuum-pump connected to the waste reservoir.

30. Apparatus for performing laboratory tests automatically according to claim 1, characterized by a system of covers for closing the apparatus at the top, comprising an independent door for access to the first region, an independent cover for access to the second region, a door which can be lowered, disposed in the front portion of the apparatus for access to reservoirs and tanks for washing solutions, and an independent door to the container holding reagents, the door for access to the first region sliding towards the interior of the machine so that, in the door's open position, the door is interposed between the two regions of the apparatus, enabling loading to be performed without risk to the user.

31. Apparatus for performing laboratory tests automatically according to claim 30, characterized in that the door for access to the first region and to the region for the feeding of the reagents, have safety locks which allow the doors to be selectively opened.

32. Apparatus for performing laboratory tests automatically according to claim 31, characterized in that the cover of the second region de-activates any movement inside the apparatus when the cover is opened.

33. Apparatus for performing laboratory tests automatically according to claim 1, characterized in that the series of storage containers have an elongate molded structure and a cross-section which decreases from the front portion towards the rear portion, their front and rear ends being molded to achieve, in the front portion, the inlet and outlet of liquid as well as selective connection to at least one of pressurized fluids and a vacuum source, whereas, at the rear end, the container is supported on a loading cell for enabling the degree of filling of the container to be read and also has an upper outlet for a connector for fluids and a lower step for bearing on the loading cell.

34. Apparatus for performing laboratory tests automatically according to claim 33, characterized in that the front end of the container has a lower front outlet for a connector for the outlet of liquid and a further two upper connections for liquid-inlet connectors being connectable to pressurized-fluids, a vacuum source, the container further having a large inlet with a threaded lid for selective access to the container.

35. Apparatus for performing laboratory tests automatically according to claim 34, characterized in that all of the connections for tubes have incorporated valves which close automatically and which can receive quick-fit connectors of the corresponding tubes.

36. Apparatus for performing laboratory tests automatically according to claim 33, wherein the front end has a large molded recess with its upper portion shaped as a handle for the handling of the container.

37. Apparatus for performing laboratory tests automatically according to claim 33, wherein the front end of the container has molded supports in its lower portion for supporting the container without rolling.

38. Apparatus for performing laboratory tests automatically according to claim 33, characterized in that the rear step for bearing on the loading cell has at least one of a chamfered and curved region for enabling the container to enter a housing by being pushed from the front.

* * * * *